(12) United States Patent
LaBorde

(10) Patent No.: US 9,977,865 B1
(45) Date of Patent: May 22, 2018

(54) SYSTEM, MEDICAL ITEM INCLUDING RFID CHIP, SERVER AND METHOD FOR CAPTURING MEDICAL DATA

(71) Applicant: Brain Trust Innovations I, LLC, Alpharetta, GA (US)

(72) Inventor: David LaBorde, Alpharetta, GA (US)

(73) Assignee: Brain Trust Innovations I, LLC, Alpharetta, GA (US)

( * ) Notice: Subject to any disclaimer, the term of this patent is extended or adjusted under 35 U.S.C. 154(b) by 0 days. days.

(21) Appl. No.: 15/816,966

(22) Filed: Nov. 17, 2017

Related U.S. Application Data

(63) Continuation-in-part of application No. 15/592,116, filed on May 10, 2017, now Pat. No. 9,848,827, which is a continuation of application No. 15/390,695, filed on Dec. 26, 2016, now Pat. No. 9,679,108, which is a continuation of application No. 15/004,535, filed on Jan. 22, 2016, now Pat. No. 9,569,589.

(60) Provisional application No. 62/113,356, filed on Feb. 6, 2015.

(51) Int. Cl.
*G06F 19/00* (2018.01)
*G06N 3/04* (2006.01)
*G06N 3/08* (2006.01)
*G06K 7/10* (2006.01)

(52) U.S. Cl.
CPC ....... *G06F 19/323* (2013.01); *G06K 7/10366* (2013.01); *G06N 3/04* (2013.01); *G06N 3/08* (2013.01)

(58) Field of Classification Search
CPC ........... G06K 7/10366; G06K 7/10009; G06K 7/10316; G06K 19/0723; G06K 7/10356; G06K 19/0717; G06K 7/0008; G06K 7/10128
USPC ....................................................... 340/10.1
See application file for complete search history.

(56) References Cited

U.S. PATENT DOCUMENTS

| 5,535,141 | A | 7/1996 | Lussi |
|---|---|---|---|
| 7,388,506 | B2 | 6/2008 | Abbott |
| 7,479,887 | B2 | 1/2009 | Meyer |
| 7,518,502 | B2 | 4/2009 | Austin et al. |
| 7,586,417 | B2 | 9/2009 | Chisholm |

(Continued)

OTHER PUBLICATIONS

Pivato et al., "Experimental Assessment of a RSS-based Localization Algorithm in Indoor Environment", [online], May 2010 [retrieved on Sep. 4, 2015]. Retrieved from the Internet: <http://www.researchgate.net/profile/Paolo_Pivato/publication/224146714_Experimental_Assessment_of_a_RSS-based_Localization_Algorithm_in_Indoor Environment/links/0912f502b6b29f22ea000000.pdf>.

(Continued)

*Primary Examiner* — Mark Blouin
(74) *Attorney, Agent, or Firm* — Culpepper IP, PLLC; Kerry S. Culpepper

(57) ABSTRACT

A system includes a plurality of RFID chips affixed to a medical item, a data collection engine device, and a server device. The data collection engine wirelessly transmits power to a first one of the RFID chips and receives first medical data from the first RFID chip while the first RFID chip is activated by the power receiver. The data collection engine generates a first message indicative of the first medical data to be sent to the server device. The server device can determine aspects of the medical item based upon the first medical data.

18 Claims, 28 Drawing Sheets

(56) References Cited

U.S. PATENT DOCUMENTS

| | | | |
|---|---|---|---|
| 7,772,981 B1 | 8/2010 | Lambert et al. | |
| 7,850,893 B2 | 12/2010 | Chisholm et al. | |
| 7,852,221 B2 * | 12/2010 | Tuttle | G06K 7/10346 340/10.1 |
| 7,875,227 B2 | 1/2011 | Chisholm | |
| 7,922,961 B2 | 4/2011 | Chisholm et al. | |
| 7,973,664 B1 | 7/2011 | Lambert et al. | |
| 8,097,199 B2 | 1/2012 | Abbott et al. | |
| 8,098,162 B2 | 1/2012 | Abbott et al. | |
| 8,120,484 B2 | 2/2012 | Chisholm | |
| 8,181,875 B2 * | 5/2012 | Nishido | G06K 19/0701 235/451 |
| 8,212,226 B2 | 7/2012 | Chisholm | |
| 8,296,247 B2 | 10/2012 | Zhang et al. | |
| 8,414,417 B2 | 4/2013 | Sato | |
| 8,478,535 B2 | 7/2013 | Jojic et al. | |
| 9,224,124 B2 | 12/2015 | Rahim et al. | |
| 9,523,534 B2 | 12/2016 | Paydar et al. | |
| 9,642,967 B2 * | 5/2017 | Ribble | G06F 19/3418 |
| 2010/0190436 A1 | 7/2010 | Cook et al. | |
| 2011/0202170 A1 | 8/2011 | Dawes et al. | |
| 2011/0291809 A1 | 12/2011 | Niemiec | |
| 2013/0002034 A1 | 1/2013 | Onizuka et al. | |
| 2015/0317589 A1 | 11/2015 | Anderson et al. | |
| 2016/0092640 A1 | 3/2016 | Caputo et al. | |

OTHER PUBLICATIONS

Zafari et al., Micro-location for Internet of Things equipped Smart Buildings, [online], Jan. 7, 2015 [retrieved on Sep. 3, 2015]. Retrieved from the Internet<URL:http://arxiv.org/abs/1501.01539>.

Bolic et al., "Proximity Detection with RFID: A Step Toward the Internet of Things", Apr. 23, 2015, Pervasive computing IEEE, vol. 14 Issue:2, Published by IEEE.

Wong et al., "30 Years of Multidimensional Multivariate Visualization", [online], 1997 [retrieved on Aug. 12, 2016]. Retrieved from the Internet: http://citeseerx.ist.psu.edu/viewdoc/download?doi=10. 1.1.30.4639&rep=rep1&type=pdf>.

Impinj, White Paper "New Thinking on an Old Challenge: Improving Healthcare Asset Management with RAIN RFID Technology", [online], 2017 [retrieved on Nov. 16, 2017]. Retrieved from the Internet: <https://www.impinj.com/media/2046/impinj-healthcare-asset-management-white-paper.pdf>.

Erica Drazen, "Using Tracking Tools to Improve Patient Flow in Hosptals", [online], Apr. 2011 [retrieved on Feb. 15, 2018]. Retrieved from the Internet: <https://www.chcf.org/publication/using-tracking-tools-to-improve-patient-flow-in-hospitals/>.

* cited by examiner

920

Event 1: Medical Item ID Removed from Package, Time of Removal, Location of Removal, Package in Disposal Time, Location
Event 2: Medical Item Used by ID of Medical Professional at Start Time, Location, End Time
Event 3: Medical Item Used for Patient ID at Start Time, Location, End Time
Event 4: Medical Item Disposed at Time, Location

DCE

940

Medical Item ID Consumed by Actor ID on Behalf of Patient ID

Server

FIG. 9G

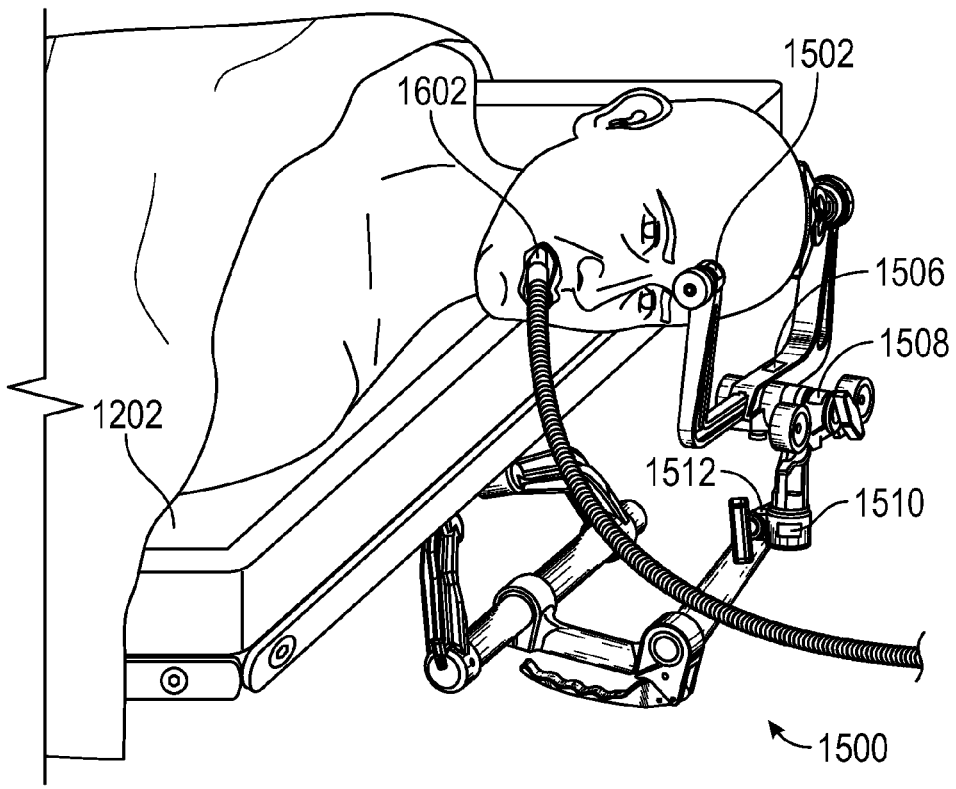
FIG. 17
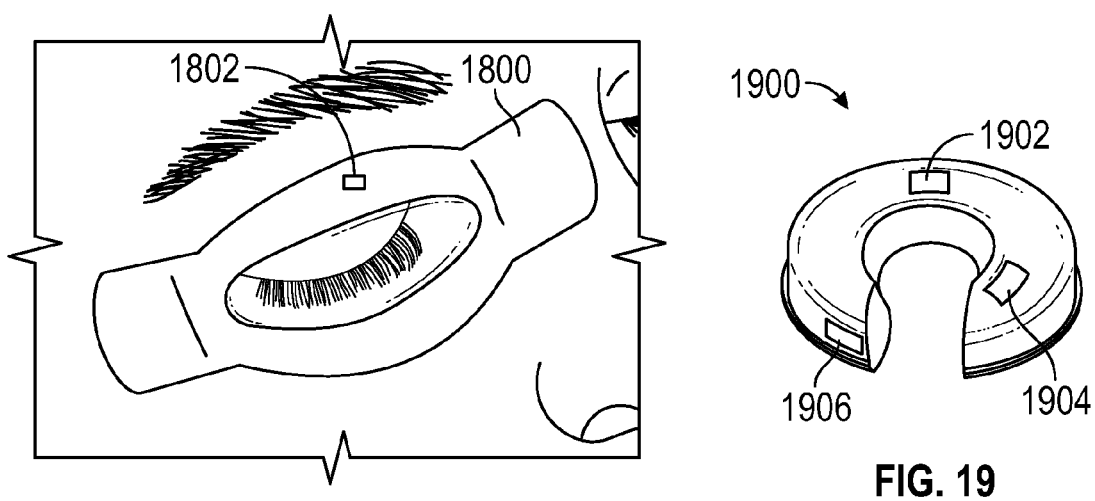
FIG. 18
FIG. 19

SYSTEM, MEDICAL ITEM INCLUDING RFID CHIP, SERVER AND METHOD FOR CAPTURING MEDICAL DATA

CROSS-REFERENCE TO RELATED APPLICATIONS

The present application is a continuation-in-part of U.S. patent application Ser. No. 15/592,116 filed on May 10, 2017, which is a continuation of U.S. patent application Ser. No. 15/390,695 filed on Dec. 26, 2016 (now U.S. Pat. No. 9,679,108), which is a continuation of U.S. patent application Ser. No. 15/004,535 filed on Jan. 22, 2016 (now U.S. Pat. No. 9,569,589), which claims the benefit of U.S. Provisional Patent Application No. 62/113,356 filed on Feb. 6, 2015, the contents all of which are incorporated herein by reference.

The present application incorporates by reference the contents of: U.S. Pat. No. 9,523,534 to Akbar Paydar et al.; U.S. Pat. No. 9,224,124 to Muhammad R. Rahim et al.; U.S. Pat. No. 8,414,417 to Suneil Mandava et al.; U.S. Patent Publication No. 20160092640 to Jimmy C. Caputo et al.; U.S. Patent Publication No. 2011/0202170 to Dennis K. Dawes et al.; U.S. Pat. No. 7,518,502 to Gene Edward Austin et al.; and U.S. Pat. No. 5,535,141 to Andre Lussi.

TECHNICAL FIELD

The technical filed generally relates to a system including one or more medical devices and items including radio-frequency identification chips, and a server.

BACKGROUND

Medical facilities utilize or consume medical devices and other consumable items in the course of providing patient care. Examples items include catheters, medication, surgical implants, sterile wrappings, sterile gowns, sterile gloves, surgical operation sponges, stethoscopes, endoscopes, endotracheal tubes, etc. Some medical items are used only one time during a procedure, while others may be used repeatedly after proper sterilization procedures, etc. The medical items may be stored or be present within medical devices such as storage cabinets, refrigerators, trays, autoclave machines, etc. All of these types of medical items or devices will be referred to herein sometimes as medical items for the sake of brevity. Medical facilities usually have procedures for these types of medical items.

SUMMARY

A Radio-frequency Identification (RFID) chip can transmit information to a reader in response to an interrogation signal or polling request from the reader. Exemplary readers include the reader described in U.S. Pat. No. 7,518,502. The RFID chip can be incorporated in a tag (RFID tag) which is placed on a medical consumable item so that information can be passively captured. An RFID tag can be an active-type with its own power source, or a passive-type or battery-assisted passive type with no or limited power source. Both the passive-type and battery-assisted passive type will be referred to here as passive-type for sake of brevity. Placing an active-type RFID tag on some medical items may not be feasible because of financial considerations, weight, etc. On the other hand, placing a passive-type RFID tag on medical items may be more feasible; however, a power source will be needed to passively obtain information. Therefore, a device that can provide power to the RFID as well as obtain the information from the RFID tag would be beneficial for activity based costing and to ensure proper charging.

During medical procedures such as surgery, it is very important to avoid errors such as using instruments that have not been properly sterilized, retaining the medical item in the patient after conclusion, performing surgery on the wrong section of the body, performing the wrong surgical procedure or even performing surgery on the wrong patient. Some of these errors are commonly referred to as "surgical never events". In order to avoid surgical never events, the position of a medical item, a patient with respect to the medical item, as well as the medical items consumed are desirable information.

Prior to surgery, it is also very important to confirm that the necessary instruments (medical items) are in the operating room. A medical facility may have a system in which surgical preference cards define the resources and preferences for specific procedures, including surgical materials, equipment, instructions, and setup. Not having the necessary equipment, instruments, etc. can be a source of delay or inability to handle emergencies that may arise.

Medical items such as code carts include emergency medication/equipment for life support protocols. If a code cart does not have the necessary equipment/medication when a code is called (i.e., a cardiac arrest for example), an unnecessary death may occur.

Some medical instruments (items) are sterilized between uses by, for example, an autoclave machine (another type of medical item). It is important to monitor when medical instruments were properly sterilized.

Some medical items such as medicines, blood/tissue must be stored in temperature controlled storage environments such as refrigerators. It is important to monitor the temperature of such refrigerators to make sure it is in accordance with the desired parameters for the medical products. Further, access controls to prevent or hinder unauthorized individuals from accessing the refrigerator and/or medical products are also beneficial.

In view of the above problems, as well as other concerns, the present disclosure concerns a system for capturing medical data from a medical item which includes an RFID chip.

According to various embodiments, the system includes a data collection engine (DCE), a plurality of RFID chips associated with a plurality of medical items and or locations, and a server device.

The DCE includes a power transmission subsystem, a transceiver, a controller operatively coupled to the transceiver, and a memory including instructions for configuring the controller. The power transmission subsystem includes a power source and an antenna arranged to wirelessly transmit power to a passive-type RFID chip. The transceiver can communicate with a server device via a connection to a network such as a LAN, the Internet, or cellular network and also wirelessly communicate with RFID chips. The controller is configured to generate messages to be sent by the transceiver to the server device. The DCE can also communicate with a client device such as a smartphone. Rather than a DCE, or in conjunction with the DCE, the system can include a mobile device reader for sending an interrogation signal to the RFID chips and receiving a message in reply to the interrogation signal including a date and time stamp denoting the moment at which the interrogation transaction occurred. The DCE can be a fixed unit fixed to the ceiling of a room or a mobile reader for providing the power to the RFID tags by the interrogation signal.

The RFID chips can be incorporated in tags (RFID tags) which are placed on the medical items so that information can be passively captured. The RFID tags can be associated with following exemplary medical items: an identification badge; a patient wrist band; a trash receptacle, spine instrumentation that measures information about the stress/force/moment at native human/implant interfaces; endoscopes; medical catheters; sponges to assist with sponge count at end of an operation and to ensure that no sponge is left in the patient; hospital beds; surgical drain tip; refrigerated storage units; endoscope cabinets; instrument trays; storage cabinets; autoclave machines, physical locations within hospital facilities, etc.

The RFID tag includes an antenna for communicating with the DCE or mobile device reader, other RFID tags and/or a client device such as a smartphone. If the RFID tag is passive-type, the antenna wirelessly receives power from, for example, the DCE, another RFID tag or the client device. The RFID tag further includes a controller configured by a memory, a microcontroller or dedicated logic for generating messages to be transmitted and a sensor group.

The server device includes a transceiver, a controller coupled to the transceiver, and memory portions including instructions for configuring the controller and providing one or more databases related to the medical consumable items. The transceiver can communicate with the DCE via a connection to the network.

The system can be deployed for a single tenant (enterprise or private cloud deployment) and/or shared across multiple facilities (multi-tenant cloud deployment).

In the system according to a first embodiment, RFID tags send medical data to a DCE, the date and time of this transaction is captured, the DCE transmits messages indicative of the medical data to the server device, which stores the medical data in one or more databases. A client device can request data retrieval of certain medical data from the server. Moreover, a plurality of events can be determined on the RFID chip level.

According to an aspect, a first RFID chip, which is a passive-type RFID chip, is activated by power received from the power transmission subsystem of the DCE or of another RFID chip. While activated by the received power, the first RFID chip transmits first medical data indicative of a first event which is received by the transceiver of the DCE. The date and time of the RFID and DCE communication is also captured. The controller of the DCE is configured to generate a first message indicative of the first medical data to be sent by the transceiver to the server device via a network connection immediately or at a later time, for example if a network connection is not currently available. A date and time stamp denoting the date and time of the communication between the server and the DCE is captured and stored by the server, in addition to the date and time stamp of the message transaction(s) between RFID chips and the DCE.

According to an aspect, the transceiver of the DCE can receive identification data from the first RFID chip while the first RFID chip is activated by the received power. The controller of the DCE can be configured to store the identification data in the memory to be associated with the first RFID chip and to generate the first message to include the identification data.

According to an aspect, the transceiver of the DCE is further configured to receive second medical data from a second RFID chip which is an active-type RFID chip having its own power source. The controller of the DCE is further configured to generate a second message indicative of the second medical data to be sent by the transceiver to the server device via the network connection immediately or at a later time, for example if a network connection is not currently available. A date and time stamp denoting the date and time of the communication between the server and the DCE is captured and stored by the server, in addition to the date and time stamp of the message transaction(s) between RFID chips and the DCE.

According to an aspect, the second RFID chip can receive third medical data from a third RFID chip when the third RFID chip is more or less than a predetermined distance from the second RFID chip including the date and time stamp of the communication transaction between the second RFID chip and the third RFID chip. The second medical data received by the transceiver of the DCE according to the third aspect can further include the third medical data associated with both the second and third RFID chips and respective date and time stamps for each included communication transaction.

According to an aspect, the power transmission subsystem is further arranged to transmit power to a second passive-type RFID chip for activating the second RFID chip. The transceiver of the DCE of the first aspect receives second medical data from the second passive-type RFID chip indicative of a second event when a third RFID chip is more or less than a predetermined distance from the second passive-type RFID chip while the second passive-type RFID chip is activated by the power. The controller of the DCE is configured to generate a message indicative of the second medical data to be sent by the transceiver to the server via the network connection, immediately or at a later time, including respective date and time stamps for each communication transaction making up the data.

According to an aspect, the first RFID tag of the first aspect is associated with an identification for a medical professional or a patient, and the first medical data includes identification information of the first RFID tag, location data and a time duration in which the identification has been in a particular location.

According to an aspect, the transceiver is further configured to receive a data storage request from a client device, the data storage request including data associated with a second RFID tag coupled to the client device, and the controller is further configured to generate another message including the data storage request to be sent to the server device.

According to an aspect, the transceiver of the server device is configured to receive the message from the DCE, wherein the message from the DCE includes at least an identification associated with the first RFID tag and a date and time stamp of the communication transaction between the DCE and RFID chip; the server stores this data along with the date and time stamp of the communication between the server and DCE. The transceiver is further configured to receive an information request from a client device and to send an information reply including usage parameters associated with the first RFID tag to the client device. The server device includes one or more memory sources operatively coupled to the controller. The memory sources include a database and instructions for configuring the controller. The instructions configure the controller to: determine data in the database that is associated with the identification for the first RFID tag in the information request; generate the information reply including the usage parameters associated with the first RFID tag based upon the determined data; and store data in the message from the DCE in the database to be associated with the identification of the first RFID tag.

According to an aspect, the server device includes a transceiver configured to receive a plurality of messages from the DCE, a controller operatively coupled to the transceiver; and one or more memory sources operatively coupled to the controller, the one or more memory sources including instructions for configuring the controller to determine based upon medical events included in the plurality of messages whether a medical item associated with the first RFID tag has been consumed, whether the medical item is being stored in conditions that do not meet specified criteria, for example out of the required temperature range or at a time equal to or exceeding the expiration date, whether the medical item is in a cleaning a sterilization state that does not meet required criteria, among other determinations.

In the system according to a second embodiment, RFID tags send medical data to a DCE, which transmits messages indicative of the medical data to the server device in an immediate or delayed fashion, and the server device stores the medical data in a database. The server device and/or the DCE and/or another entity can determine whether events such as a never event, a consumption event, and/or a charging event, storage not meeting criteria event, use in an out of compliance cleaning or sterilization state, or other event (all referred to here as the event) has occurred based upon the medical data received from the RFID tags, location data, medical item data, patient data and medical professional data stored in the database. A client device can request data retrieval of certain medical data.

The server and/or the DCE can be configured to determine whether the event has occurred based upon at least the parameters in the medical data obtained from the RFID tags such as proximity to another RFID tag, duration of the proximity and orientation values, temperature values, sterilization history, etc.

According to an aspect of the second embodiment, a server device receives messages from a plurality of first RFID tags affixed to a medical item and a second RFID tag associated with an individual such as a patient, medical professional or other medical item. The first RFID tag can be a passive-type RFID tag activated by power received from the DCE or an active-type RFID tag. The second RFID tag can be a tag on a patient wristband, an identification badge, or a medical item. The server device includes a transceiver configured to receive the messages. The messages from the plurality of first RFID tags affixed to the medical item include input attributes of the medical item. The message from the second RFID tag associated with the patient can include a patient, medical professional, or medical item identification. The server device includes a controller operatively coupled to the transceiver and one or more memory sources operatively coupled to the controller.

The one or more memory sources storing a first database including a plurality of identifications associated with a plurality of patients, medical professionals, medical items, and attributes for each of the plurality of identifications.

The one or more memory sources further include instructions for configuring the controller to determine: a present orientation of the patient, medical professional, or medical item based upon the input attributes and to determine if the present orientation corresponds with one or more of the attributes associated with the patient, medical professional, or medical item in the patient database; a present state (such as temperature) of a device in which medical items are present and to determine if the present state is, for example, a dangerous temperature or in violation of compliance requirements such as a cleaning and sterilization cycle.

According to an aspect of the server device, the attributes includes a surgical procedure scheduled for a patient; and the controller is further configured to determine a present patient orientation of the patient corresponds with the surgical procedure scheduled. The attributes may also include appropriate storage temperature range for a medical item and the controller is configured to determine if the current storage temperature is in compliance. In addition, the attributes include expiration date for a medical item and the controller is configured to determine whether the medical item is expired. Furthermore the attributes might include historical knowledge of the cleaning and sterilization cycle for a medical item and the controller is configured to determine whether current use is out of compliance with cleaning and sterilization cycle requirements. The above are exemplary, but not all inclusive of the determinations the server's controller is configured to make.

According to an aspect of the server device, the one or more memory sources store a second (medical professional) database including medical professional identifications associated with medical professionals, and attributes related to each of the medical professional identifications, and the plurality of messages further include an indication that a third RFID tag associated with one of the medical professionals is less than a predetermined distance from the second RFID tag associated with the one patient.

According to an aspect of the server device, the one or more memory sources store a medical item database including medical item identifications associated with different medical items, and attributes related to each of the medical item identifications, and the plurality of messages further include an indication that a third RFID tag associated with one of the medical items is less than a predetermined distance from the second RFID tag associated with the one medical item.

According to an aspect, the server device receives the one or more messages from a DCE via a connection to a network, the DCE includes: a power transmission subsystem including a power source and an antenna arranged to wirelessly transmit power from the power source to one or more of the plurality of first RFID tags; a transceiver configured to receive first medical data from one or more of the plurality of first RFID tags and the patient or medical item identification of the second RFID tag associated with the patient or medical item, the medical data including the input attributes of the plurality of first RFID tags; a controller operatively coupled to the transceiver; and one or more memory sources operatively coupled to the controller, the one or more memory sources including instructions for configuring the controller to generate a first message indicative of the first medical data to be sent by the transceiver to the server via a network connection.

According to an aspect, the server device is configured to use a trained model such as a Neural Network Model (NNM) to predict an event based upon the input attributes received from the RFID tags to, for example, determine if the patient is in a correct position based.

It should be noted that all or some of the aspects of the first and second embodiments can be combined.

BRIEF DESCRIPTION OF THE DRAWINGS

The accompanying figures, in which like reference numerals refer to identical or functionally similar elements, together with the detailed description below are incorporated in and form part of the specification and serve to further illustrate various exemplary embodiments and explain various principles and advantages in accordance with the present invention.

FIGS. 9A-9G illustrate an exemplary operating environment in which one or more DCEs receive medical data from RFID chips associated with medical items, medical professionals and a patient according to the first embodiment.

FIG. 17 is a diagram illustrating a patient on an operating table including the skull clamp headrest of FIG. 15A and the endotracheal tube of FIG. 16A.

FIG. 18 is a diagram illustrating an adhesive eyelid occlusive dressing including an RFID chip according to the second embodiment.

FIG. 19 is a perspective view of a horse-shoe headrest including a plurality of RFID chips according to the second embodiment.

DETAILED DESCRIPTION OF PREFERRED EMBODIMENTS

In overview, the present disclosure concerns a Data Collection Engine (DCE), RFID chips for medical items and for identification tags of medical professionals and patients, and a server device.

The instant disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

It is further understood that the use of relational terms such as first and second, and the like, if any, are used solely to distinguish one from another entity, item, or action without necessarily requiring or implying any actual such relationship or order between such entities, items or actions. It is noted that some embodiments may include a plurality of processes or steps, which can be performed in any order, unless expressly and necessarily limited to a particular order; i.e., processes or steps that are not so limited may be performed in any order.

Reference will now be made in detail to the accompanying drawings. Wherever possible, the same reference numbers will be used throughout the drawings to refer to the same or like parts.

Figure 1:
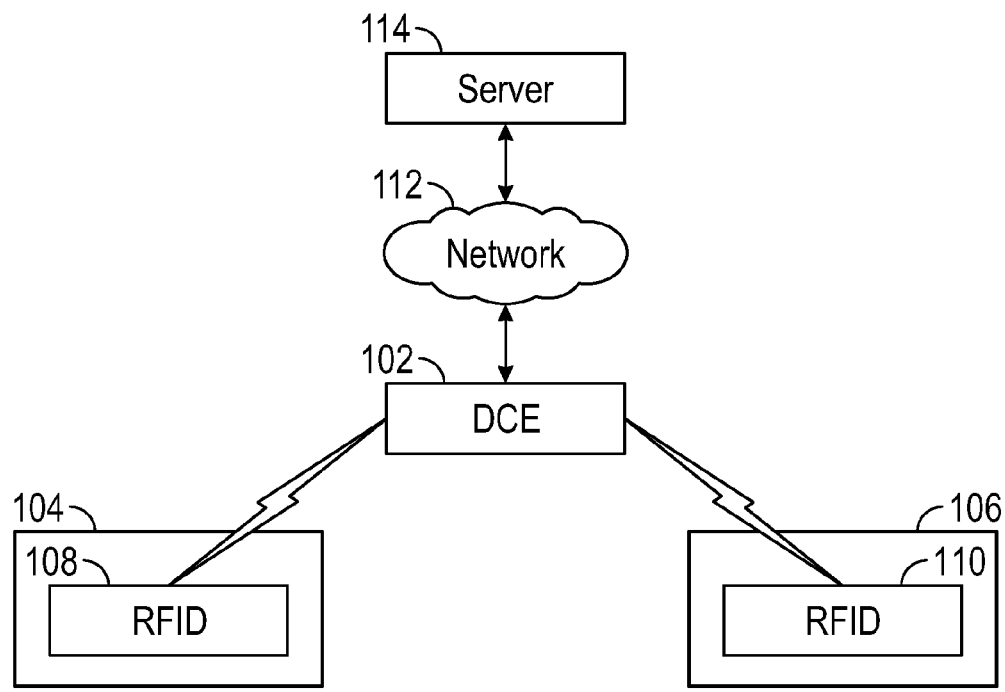
FIG. 1 illustrates an exemplary operating environment in which a Data Collection Engine (DCE) receives medical data from RFID chips associated with medical items and transmits the medical data to a server via a connection to a network according to exemplary embodiments.

Referring to FIG. 1, an exemplary operating environment in which the system according to various embodiments can be implemented will be discussed. The environment includes a DCE 102 communicating with a first RFID chip 108 disposed in a first room 104 and a second RFID chip 110 disposed in a second room 106. Each of the RFID chips 108, 110 is associated with a medical item. As discussed more fully below, the communication between the RFID chips 108, 110 and the DCE 102 is preferably wireless; however, wireline communication or a combination of wireless and wireline communication can also be used in some cases. The DCE 102, although shown here as a single entity, can include sub-portions in each of the rooms 104, 106. The DCE 102 communicates with one or more server devices represented generally by server 114 via a connection to a network 112 such as a local area network (LAN), wide area network (WAN), the Internet, etc. The first and second rooms 104, 106 can be, for example, separate rooms of a hospital facility. The communication between the DCE 102 and the RFID chips 108, 110 and/or between the DCE 102 and the server 114 can be encrypted or unencrypted. The network 112 can be, for example, a private LAN for the hospital facility. The server 114 can be a computing device local to the hospital facility. On the other hand, the network 112 can be the Internet, the DCE 102 can be local to the hospital facility and the server 114 can be one or more remote computing devices. The DCE 102 can be a reader device such as, for example, the TSL 1128 Handheld RAIN RFID reader made by IMPINJ™. One of ordinary skill in the art should appreciate that the server 114 can represent entities necessary for providing cloud computing such as infrastructure and service providers.

Figure 2:
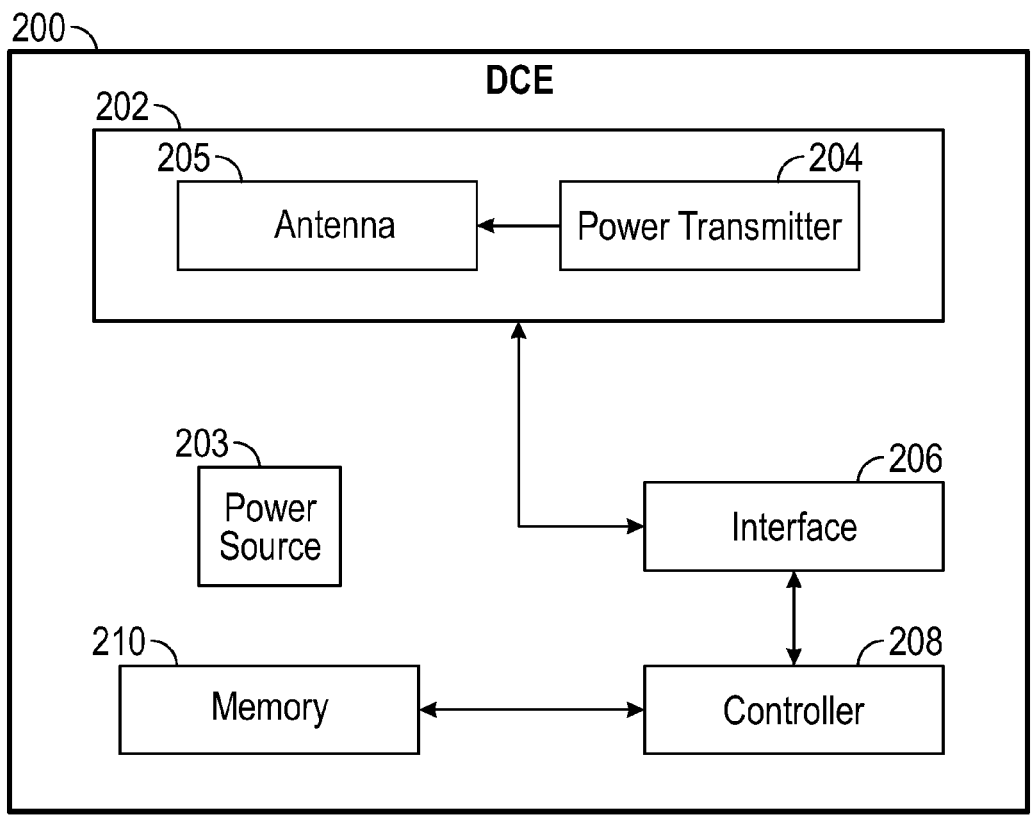
FIG. 2 is a block diagram illustrating exemplary portions of the DCE according to exemplary embodiments.

Referring to the block diagram of FIG. 2, portions of an exemplary DCE 200 will be discussed. The DCE 200 includes a transceiver 202, a power source 203, an interface 206, a controller 208 and one or more memory portions depicted by memory 210.

Referencing the Open Systems Interconnection reference model (OSI model), the transceiver 202 can provide the physical layer functions such as modulating packet bits into electromagnetic waves to be transmitted and demodulating received waves into packet bits to be processed by higher layers (at interface 206). The transceiver 202 can include an antenna portion 205, and radio technology circuitry such as, for example, ZigBee, Bluetooth and WiFi, as well as an Ethernet and a USB connection. The transceiver 202 also includes a wireless power transmitter 204 for generating a magnetic field or non-radiative field for providing energy transfer from the power source 203 and transmitting the energy to, for example, an RFID chip by antenna portion 205. The power transmitter 202 can include, for example, a power transmission coil. The antenna portion 205 can be, for example, a loop antenna which includes a ferrite core, capacitively loaded wire loops, multi-turn coils, etc. In addition to energy transfer, the transceiver portion 202 can also exchange data with the RFID chip. Data transmission can be done at, for example, 1.56 MHz. The data can be encoded according to, for example, Amplitude Shift Keying (ASK). The transceiver 202 includes a power transmission system composed of the antenna 205 and the power transmitter 204.

The interface 206 can provide the data link layer and network layer functions such as formatting packet bits to an appropriate format for transmission or received packet bits into an appropriate format for processing by the controller 208. For example, the interface 206 can be configured to encode or decode according to ASK. Further, the interface 206 can be configured in accordance with the 802.11 media access control (MAC) protocol and the TCP/IP protocol for data exchange with the server via a connection to the network. According to the MAC protocol, packet bits are encapsulated into frames for transmission and the encapsulation is removed from received frames. According to the TCP/IP protocol, error control is introduced and addressing is employed to ensure end-to-end delivery. Although shown separately here for simplicity, it should be noted that the interface 206 and the transceiver 202 may be implemented by a network interface consisting of a few integrated circuits.

The memory 210 can be a combination of a variety of types of memory such as random access memory (RAM), read only memory (ROM), flash memory, dynamic RAM (DRAM) or the like. The memory 210 includes instructions for configuring the controller 208 to execute processes such as generating messages representative and indicative of medical data and events received from RFID chips and/or determining the occurrence of one or more events as discussed more fully below.

The controller 208 can be a general purpose central processing unit (CPU) or an application specific integrated circuit (ASIC). For example, the controller 208 can be implemented by a 32 bit microcontroller. The controller 208 and the memory 210 can be part of a core (not shown).

Figure 3A:
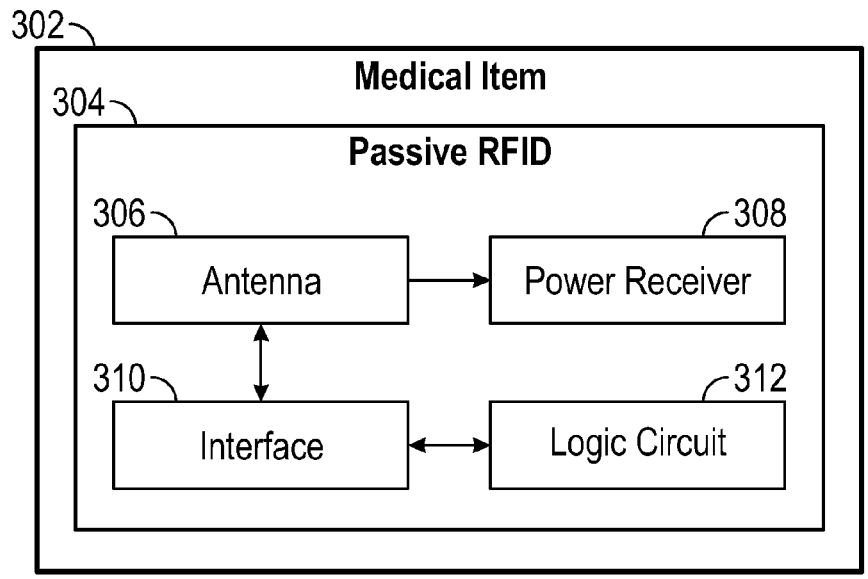
FIG. 3A is a block diagram illustrating exemplary portions of a passive-type RFID chip associated with a medical item according to exemplary embodiments.

Referring to FIG. 3A, portions of an exemplary passive-type RFID chip 304 will be discussed. The RFID chip 304 can include an antenna portion 306, a power receiver 308, an interface 310 and a logic circuit 312. The antenna portion 306 can be a loop antenna which includes a ferrite core, capacitively loaded wire loops, multi-turn coils, etc., similar to the antenna portion 205 of the DCE. The power receiver 308 can include a power receiving coil for receiving power from the power transmission coil of the power transmitter 202 by electromagnetic coupling. The power receiver 308 can provide power to the chip 304 and/or charge a power source (not shown) such as a battery.

Generally, the logic circuit 312 generates medical data such as an identification of the RFID chip 304 and/or the medical item to which the chip is affixed, state, location, date, time, and changes in any data or properties thereof over time, all of which will be referred to as medical data. It should be noted that the medical data includes situational data which refers to a) the identity of the RFID chip, the identity reference for an individual, facility plant, property, equipment to which the RFID chip is affixed, and b) the distance between an RFID chip and other RFID chips, the distance between the RFID chip and the DCE, the distance between the RFID and client device such as smartphone or mobile reader device, the identity and any identity references of the other RFID chips, DCEs and mobile client devices (i.e. smartphones) with which the RFID communicates, and any obtained from a sensor associated with i) the RFID chip or ii) another RFID chip, or client device (i.e. smartphone) with which the RFID communicates. Examples of the sensor data might be location in three dimensions, acceleration or velocity, displacement relative to some reference, temperature, pressure, etc.

The medical data can also include data indicative of an event such as, for example, near field communication (NFC) established with the DCE or another RFID chip, a time duration for which the RFID chip 304 has been within a certain location, historical data, etc. Although not shown, the logic circuit 312 can include or be coupled to a non-volatile memory or other memory source.

The interface 310 can format a received signal into an appropriate format for processing by the logic circuit 312 or can format the medical data received from the logic circuit 312 into an appropriate format for transmission. For example, the interface 310 can demodulate ASK signals or modulate data from the logic circuit 310 into ASK signals.

Figure 3B:
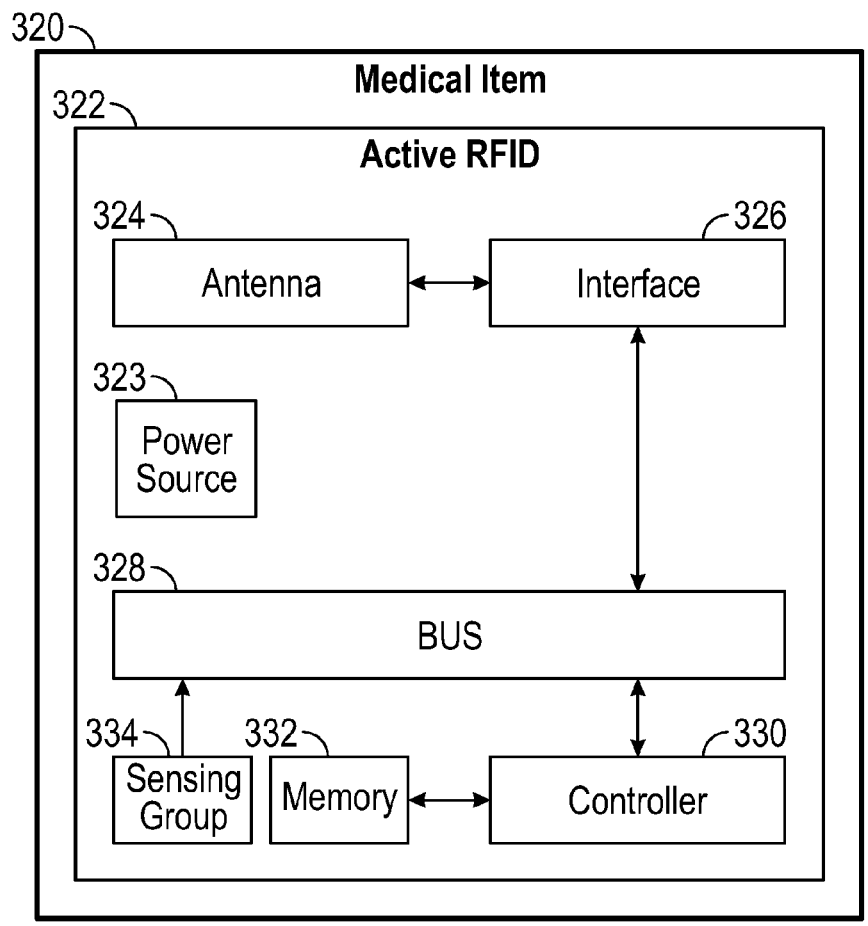
FIG. 3B is a block diagram illustrating exemplary portions of an active-type RFID chip associated with a medical item according to exemplary embodiments.

Referring to FIG. 3B, circuit-level portions of the active-type RFID chip 322 on a medical item 320 will be discussed. The RFID chip 322 can include a power source 323, an antenna portion 324, an interface 326, a bus 328, a controller 330, a memory portion 332 and a sensing group 334. The power source 323 can be, for example, a battery. Although not shown, the chip 322 can also include a power management portion coupled to the power source 323.

The antenna portion 324 and interface 326 can be similar to those of the passive-type RFID chip 304. However, it should be noted that the antenna portion 324 can receive data from other passive-type and active-type RFID chips as well as the DCE and can send this and other data to the DCE, or other RFID chips.

The sensing group 334 includes sensing portions for sensing contact, motion characteristics such as an acceleration value, whether the chip is within a predetermined distance from another RFID chip, etc, a distance from one or more other RFID chips and/or the DCE, and/or distance and angle from a base orientation. The sensing group 334 can include a temperature sensor, a set of accelerometers for determining the acceleration value of the item 320, a plurality of barometers to estimate the vertical position or to recognize vertical movements, a digital compass that collects orientation information about the item 322 which may be implemented by any number of methodologies including indoor positioning using WiFi signals based on utilizing the received signal strength (RSS) and the fingerprinting method, the Pedestrian Dead Reckoning (PDR) approach, Ultrasonic, Pseudolites, NFC, Ultra Wide Band (UWB), microphone and light sensor, an afocal optical flow sensor, camera images and range data captured by a 2D laser scanner, infrared images used to localize and track moving targets, among other approaches, a gyroscope for measuring angular rotation associated with the apparatus to provide an orientation value, a proximity sensor for detecting if the chip 322 is within a predetermined distance of another chip 322, a touch sensor layer and/or pressure sensor for sensing contact and magnitude of the pressure, and a geomagnetic sensor for sensing geomagnetic field strength. Preferably, the sensed motion characteristics include data represented in the time domain. The accelerometers can detect subtle movements along the three axial directions. The accelerometer reading, when combined with the data from the digital compass, barometer, and/or the gyroscope, can facilitate motion detection. The sensing group 334 can include a separate OpenBeacon active tag or a Sense-a-Tag as described in "Proximity Detection with RFID: A Step Toward the Internet of Things" by Bolić et al., Pervasive Computing, IEEE, (Volume 14, Issue 2), published on April-June 2015, the contents of which are incorporated herein by reference. Further, in conjunction with or separately from the proximity sensor, the sensing group can include a distance sensor for measuring a distance to a target node such as another RFID chip. The distance sensor may be a received signal strength (RSS) indicator type sensor for measuring the RSS of a signal received from a target node such as the DCE or another RFID chip. The distance from the target node can be obtained by a plurality of RSS measurements.

The controller 330 is configured according to instructions in the memory 332 to generate messages to be sent to the DCE or another chip. Particularly, the controller 330 can be configured to send a registration message which includes identification data associated with the RFID chip 322 and thus the medical item 320. Further, in a case in which the RFID chip 322 wirelessly provides power to another passive-type RFID chip, the controller 330 can be configured to generate a message including identification data associated with the passive-type RFID chip, in combination with, or separately from its own identification data to the DCE.

The controller 330 can be configured to generate messages including medical data indicative of an event. These types of messages can be sent upon receiving a request from the DCE or another entity, upon occurrence of the event, or at regular intervals. Example events include near field communication established with another RFID chip, contact detected by the sensing group 334, positional information, a time duration of such contact and position, etc. Specific examples of events will be discussed later.

It should be noted that the passive-type RFID chip can also include a sensing group or be coupled to the sensing group. For example, the RFID chip 304 can be a Vortex passive RFID sensor tag which includes a LPS331AP pressure sensor. For example, the RFID chip 304 can be a MONZA X-8K DURA or X-2K DURA tag made by IMPINJ™ which include embedded sensors. Both active and passive types of sensors can include RSS measurement indicators. The controller or control logic can determine the distance from the RSS measurements based upon localization algorithms such as, for example, Centroid Location (CL), Weighted CL, or the Relative Span Exponentially Weighted Localization (REWL) algorithm as discussed in "Experimental Assessment of a RSS-based Localization Algorithm in Indoor Environment" by Pivato et al., IEEE Instrumentation and Measurement Technology Conference, published on May 2010, the contents of which are incorporated herein by reference.

The RFID chip 302, 320 may be high-frequency (HF) tags, ultrahigh-frequency (UHF) tags, high temperature resistant, autoclave resistant, ultra low temperature resistant, repeated temperature cycle between hot and cold resistant, acid resistant, chemical resistant, abrasion resistant, gamma resistant, water resistant, types among other special application RFID chip types.

Figure 11:
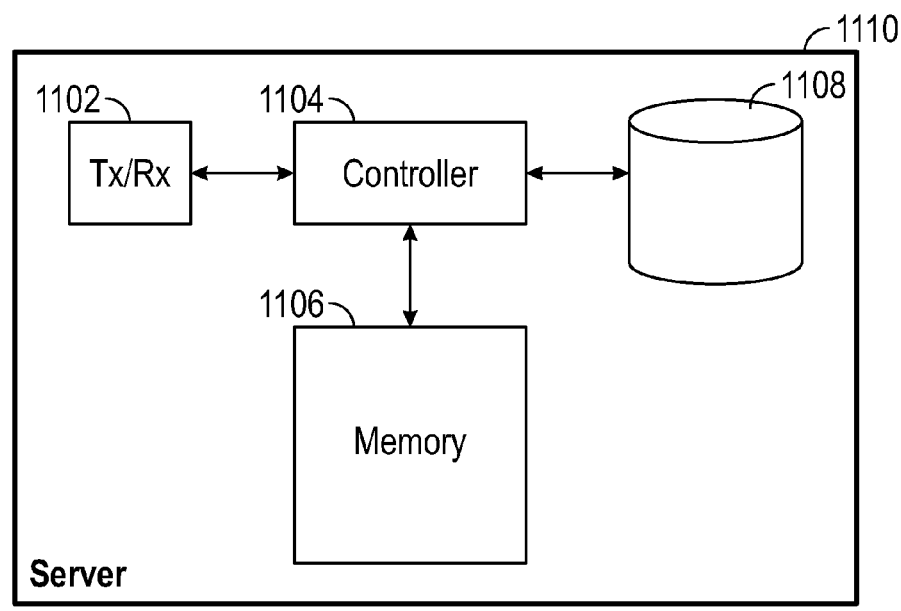
FIG. 11 is a block diagram illustrating exemplary portions of a server device according to various exemplary embodiments.

Referring to FIG. 11, the server device 1110 includes a transceiver 1102, a controller 1104, a first memory portion 1106, and one or more databases depicted generally by 1108. The databases 1108 can include a medical item database, a patient database, and a medical professional database, a location database. That database can be, for example, an atomic data store, a file system, an object database, a document oriented database, a distributed database, a block chain, a non-relational data store or NoSQL database, a relational database management system or SQL database, a key-value store, a wide-column store, a combination thereof, or other database type. The transceiver 1102 receives medical data via the network from the DCE and resource requests such as, for example, http requests, via the network, from a client device. The resource request can include verification credentials such as a token issued from a certification authority and a user name and an information request for an information reply including usage parameters associated with one or more RFID chips. The transceiver 1102 sends the information reply including the usage parameters associated with the one or more RFID chips to the client device.

The transceiver 1102 can be similar to the transceiver of the DCE.

The memory 1106 can be one or a combination of a variety of types of memory such as RAM, ROM, flash memory, DRAM or the like. Alternatively, the database 1108 can be included in the memory 1106. The memory 1106 includes instructions for configuring the controller 1104.

Among the databases 1108, the medical item database stores a plurality of medical item identifications and usage attributes associated with each of the item identifications or to which usage attributes associated with each of the item identifications stored elsewhere may be referenced. The usage attributes can include an identification of a medical professional that used the medical item, an identification of a patient for whom the medical item was used, a time duration for which the medical item was in a certain location, a series of RFID derived messages that include a date and time stamp or unique identifiers referencing said messages stored elsewhere, etc. The patient database can store patient identifications, attributes associated with each patient identification such as dispositions, scheduled surgeries, location history, consumed medical items, or references to said data stored elsewhere in a separate schema or separate information system all together, etc. The medical professional database can store medical professional identifications, attributes associated with each medical professional such as scheduled surgeries, location history, consumed medical items, etc. or a reference to said data stored elsewhere in a separate schema or a separate information system all together.

The controller 1104 is configured according to the instructions in the memory 1106 to determine data in the database 1108 that is associated with the identification for each of the one or more RFID chips in the information request; generate the information reply including the usage parameters and or a plurality of RFID derived messages previously collected and stored and data therein, associated with the one or more RFID chips based upon the determined data; and store data in the message from the DCE in the medical item database to be associated with the identification of the first RFID chip.

The controller 1104 is further configured to determine based upon medical data and events included in messages received from the DCE, whether particular events of interest are likely to have occurred such as, whether a medical consumable item has been consumed or not, and store data related to the consumption of the medical consumable item in the database 1108. The controller 1104 is further configured to determine based upon the medical data and events, and attributes in the database 1108, whether a never event has or is about to occur, and generate a message to be sent in accordance with such determination. As discussed in the second embodiment, the controller 1104 can be configured to predict values based upon a trained model such as a neural network model using machine learning to make these determinations.

The controller 1104 and database 1108 can be configured to perform command query responsibility segregation in which commands are separated from queries to allow scaling of servers that respond to queries separately from servers delegated to responding to messages. The controller 1104 and database 1108 can further be configured to use event sourcing and/or event streaming to ensure all changes to an application state get stored as a series of events which can be not only queried but reconstructed.

First Embodiment

Figure 4A:
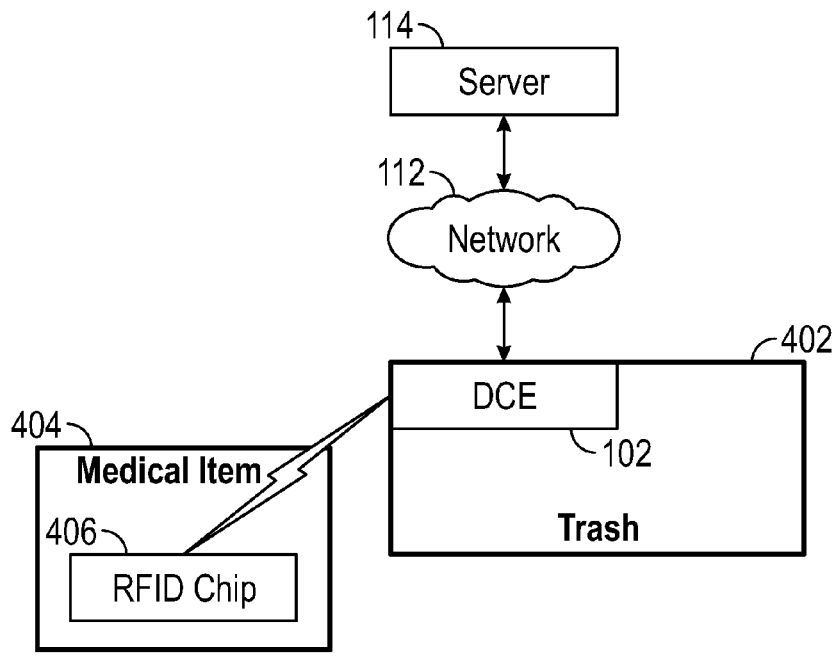
FIG. 4A-4B illustrate an exemplary operating environment in which one or more DCEs receive medical data from RFID chips associated with medical items, medical professionals and a patient according to a first embodiment.
Figure 4B:
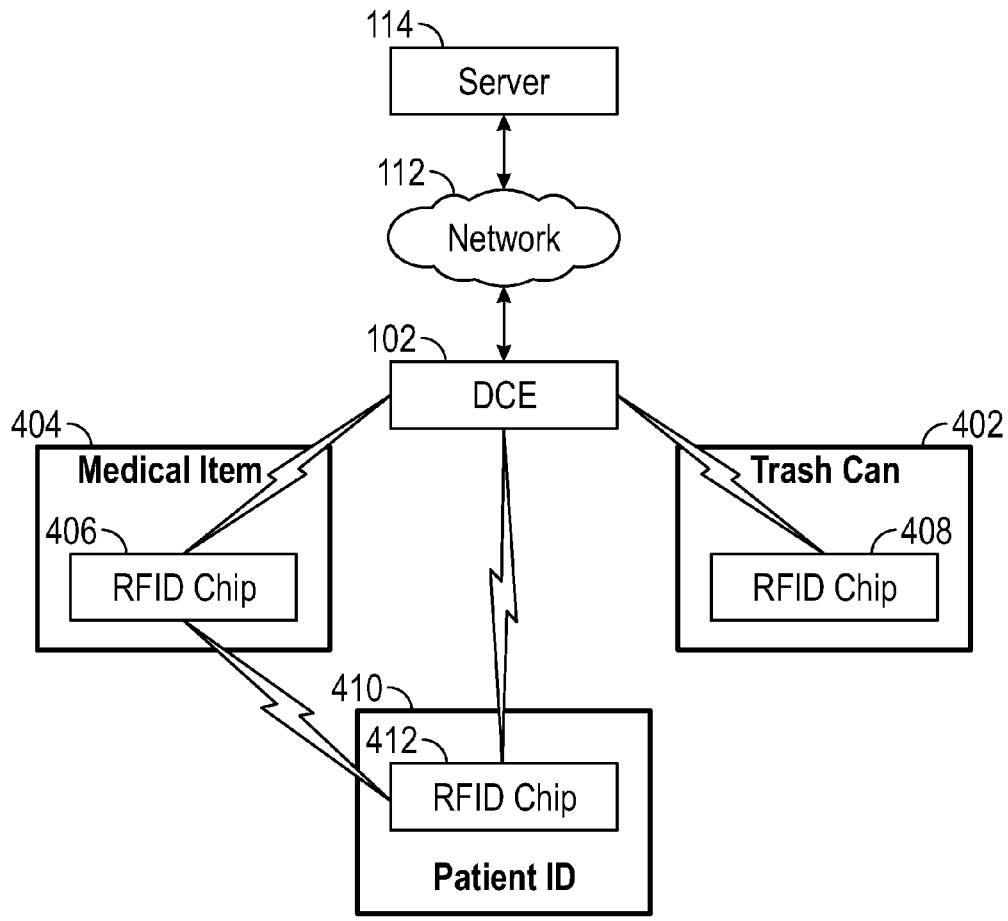

Referring to FIGS. 4A-4B, a first embodiment will be discussed by exemplary cases in which the DCE 102 receives medical data from one or more RFID chips. In the case shown in FIG. 4A, the DCE 102 is disposed on a trash receptacle 402. A medical consumable item 404 including a first RFID chip 406 (passive or active) is placed in the trash receptacle 402. The DCE 102 establishes communication with the RFID chip 406. Particularly, the DCE 102 can periodically generate a broadcast message, and receive a registration message and medical data from the RFID chip 406 indicative of a medical event in reply to the broadcast message. Alternatively, the RFID chips can self-initiate sending of the registration message periodically or in response to another external trigger If the RFID chip 406 is passive type, it can send the medical data while receiving power from the DCE 102. The registration message can include identification information associated with the RFID chip 406. In this case, the medical event would be use of the medical consumable item 404 (indicated by being in the trash receptacle 402). The DCE 102 can send a message indicative of the first medical event to be sent by the transceiver to the server device 114 via a connection to the network 112.

In the case shown in FIG. 4B, the DCE 102 is disposed not in the trash receptacle 402, but in a position such as the ceiling beneficial for establishing wireless communication coverage for a room. The DCE 102 receives medical data from the first RFID chip 406 affixed to the medical consumable item 404, a second RFID chip 408 (passive or active-type) affixed to the trash receptacle 402, and a third RFID chip 412 (passive or active-type) affixed to a patient identification 410 such as a wristband. The DCE 102 establishes communication with each of the RFID chips 406, 408, 412 by, for example, generating a general broadcast message, and receiving registration messages in reply to the broadcast message, and medical data from the RFID chips indicative of medical events. Particularly, the RFID chip 412 sends a message including medical data indicative of a first medical event, which would be the RFID chip 406 of the medical consumable item 404 being within predetermined distance from the RFID chip 412 associated with the patient identification 410. As noted above, the RFID chip (active-type or passive-type) can include a sensor for detecting near presence of another RFID chip. The RFID chip 408 sends a message including medical data indicative of a second medical event, which would be the medical consumable item 404 being within predetermined distance from the RFID chip 408 associated with the trash receptacle 402 for more than a predetermined time duration. The RFID chip 406 sends a message including medical data indicative of the chip identification. The DCE 102 can send one or more messages indicative of the medical events to be sent to the server device 114 via the network connection.

Figure 5:
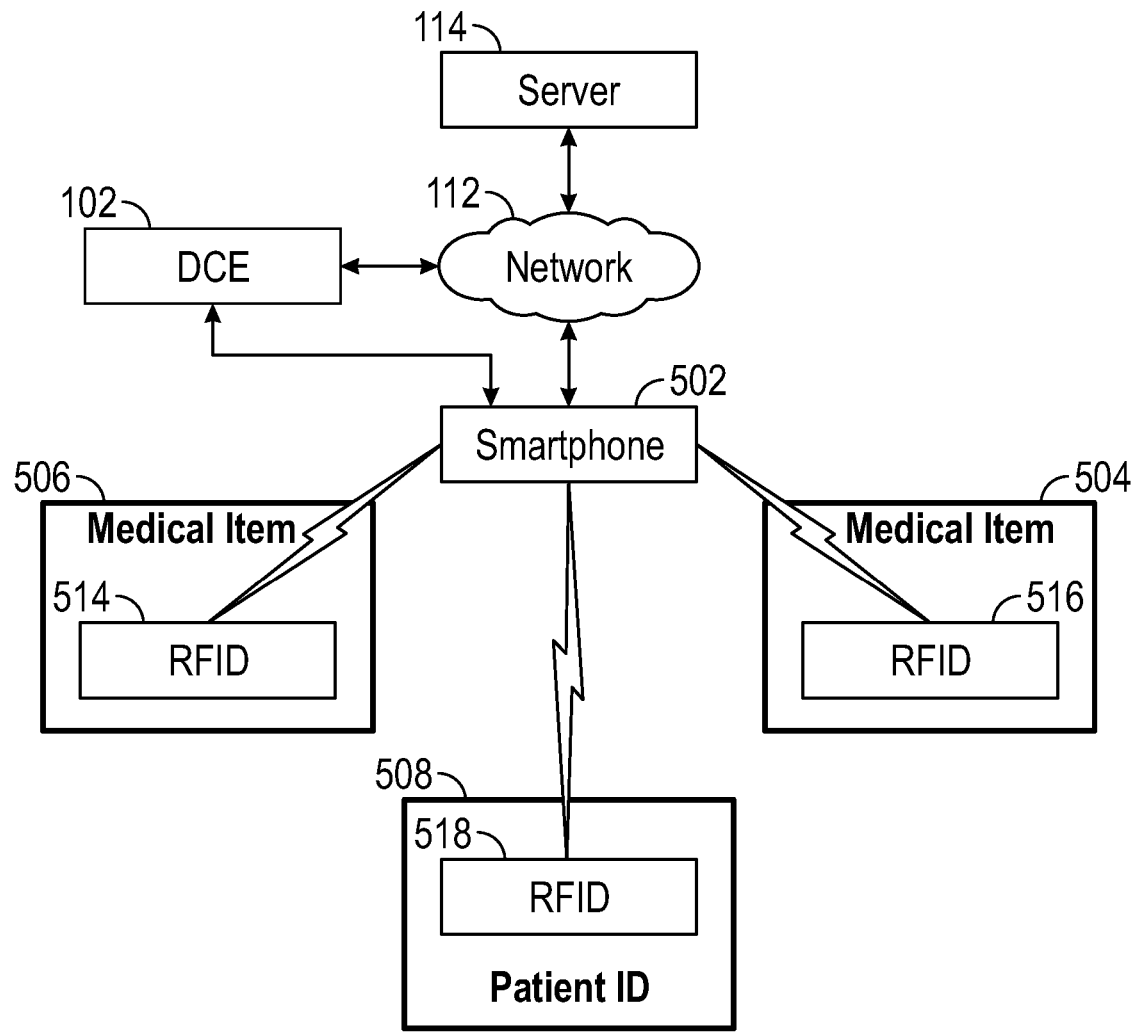
FIG. 5 illustrates an exemplary operating environment in which a smartphone receives medical data from RFID chips associated with medical items, medical professionals and a patient according to a modification to the first embodiment.

Referring to FIG. 5, exemplary modification to the first embodiment will be discussed by an exemplary operating environment in which a smartphone 502 communicates with the RFID chips. The smartphone 502 generates a broadcast message, and receives messages indicative of medical events from the RFID chips 514, 516, 518 associated with medical items 506, 504, 508. The messages include registrations messages and medical data indicative of a first, second and third medical events in reply to the broadcast message. The smartphone 502 can then send this data to the DCE 102 directly or via the network 112 or even directly to the server 114. For example, in a large facility such as a hospital, there may be areas in which there is no or very poor wireless coverage from the DCE 102. In these cases, a mobile device such as the smartphone 502 can be used to obtain medical data from chips in such areas and transmit the medical data to the DCE 102. Similar to the discussion of FIGS. 4A-4B, the events can be the RFID chips being within a predetermined distance of each other.

The smartphone 502 and/or the DCE 102 can be configured to locally persist and send the medical data to the server 114 either immediately upon collecting data or at a subsequent time after a batch of one or more pieces of data has been collected. The smartphone 502 and/or DCE 102 can purge the data sent from volatile or persistent memory immediately after successfully sending it or at a later time, either automatically or when prompted.

Figure 8:
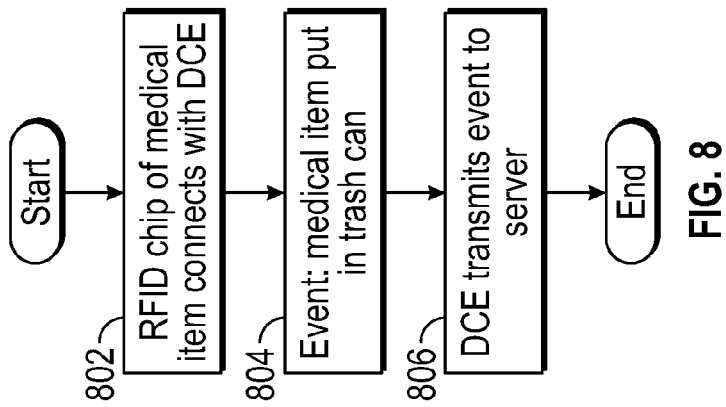
FIG. 6-8 are flow diagrams illustrating exemplary operations of the DCE and RFID chips associated with medical consumable items, medical professionals and a patient according to the first embodiment.
Figure 7:
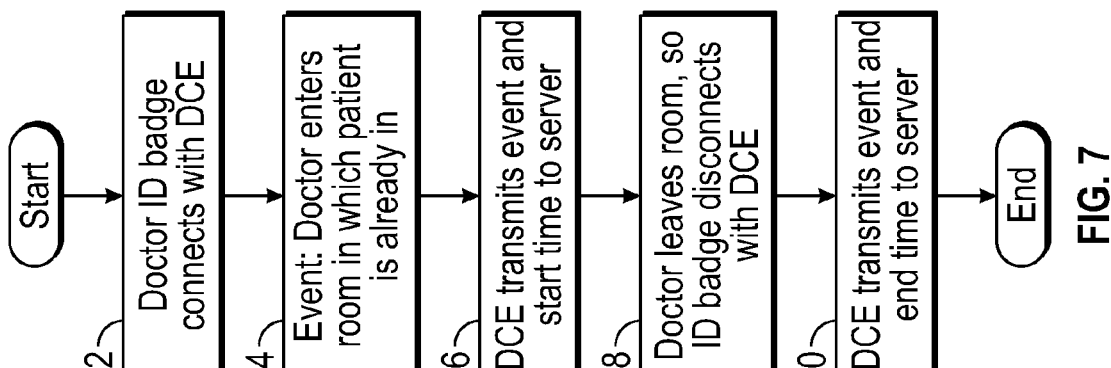
Figure 6:
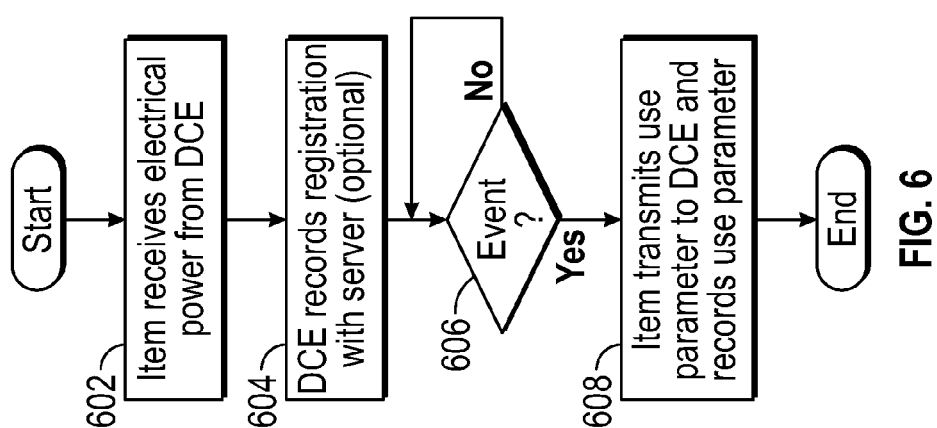

FIGS. 6-8 are flow diagrams illustrating exemplary operations of the DCE and RFID chips associated with medical items, medical professionals and a patient according to the first embodiment.

Referring to FIG. 6, the operations of the RFID chip and the DCE in a simple scenario will be discussed. At 602 a passive-type RFID chip receives electrical power wirelessly from the DCE. The wireless power can be sent along with a regular general broadcast message from the DCE or an interrogation request. Of course if the RFID chip is active-type, this step can be omitted. At 604, the RFID chip sends registration information to the DCE, which records it in its memory. Particularly, the registration information can include the identification of the RFID chip and the date and time of the registration. At 606, if the RFID chip and/or the DCE determines that an event has occurred, at 608 the RFID chip sends use parameters associated with the event to the DCE. The DCE records the usage parameters in its own memory or immediately transmits the information to the server to be stored in the medical item database. The event can be, for example, detecting that the RFID chip is within predetermined distance from another RFID chip associated with, for example, the trash receptacle for more than a predetermined time duration as discussed in FIGS. 4A-4B.

Referring to FIG. 7, the operations of the RFID chip and the DCE in a more complex scenario in which a medical professional such as a doctor meets with a patient will be discussed. At 702, the doctor wearing an identification such as a badge including an RFID chip (active or passive-type) enters a room within the communication area of the DCE and the RFID chip registers with the DCE. A patient with a patient identification including another RFID chip which has already registered with the DCE is already in the room. At 704, the DCE records a first medical event indicative of the patient and the doctor being in the same room and the start time. At 706, the DCE generates a message representative of this first medical event to be transmitted to the server. At 708, the doctor wearing the identification including the RFID chip leaves the room, and disconnects from the DCE. At 710, the DCE records the time the RFID chips disconnects as the end time of the first medical event, and generates a message representative of the end time of the first medical event to be transmitted to the server.

Referring to FIG. 8, the operations of the RFID chip and the DCE in the scenario shown in FIG. 4A will be discussed. At 802, the RFID chip associated with the medical consumable item connects with the DCE in the trash receptacle. At 804, the DCE records a medical event indicative of the medical consumable item being in the trash receptacle. At 806, the DCE generates a message representative of this medical event to be transmitted to the server.

Figure 9A:
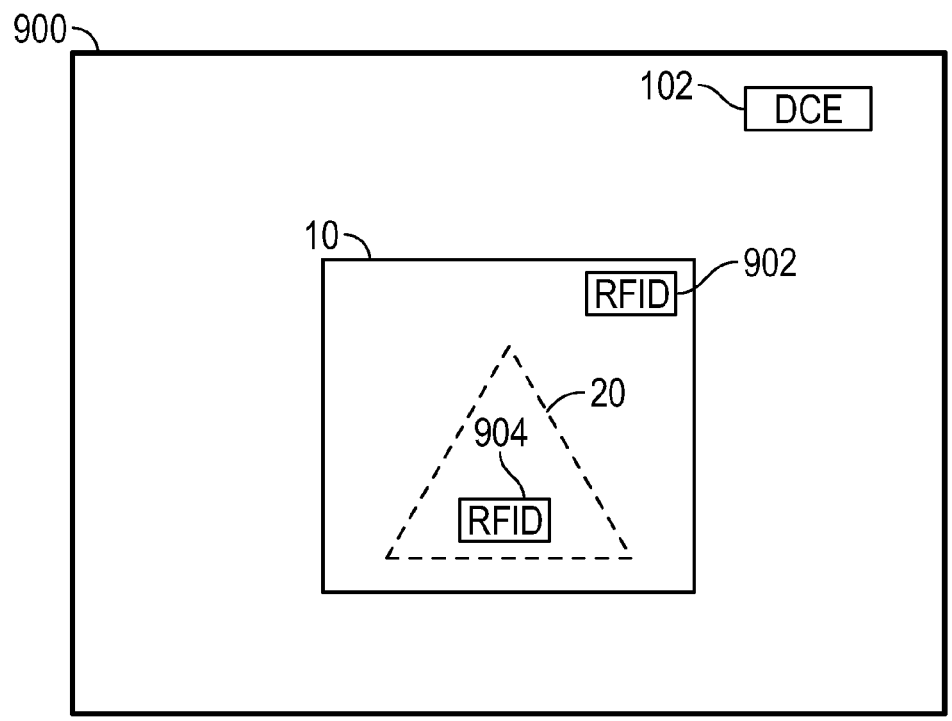

Referring to the flow diagram of FIG. 10 and the diagrams of FIGS. 9A-9G, operation of the DCE 102 and the server according to the first embodiment will be discussed. In FIG. 9A, the DCE 102 establishes a wireless communication coverage area depicted generally by room 900. A package 10 including a medical consumable item 20 is in the room 900. A first RFID chip 902 is disposed on the package 10 and a second RFID chip 904 is disposed on the medical consumable item 20 in the package.

Figure 9B:
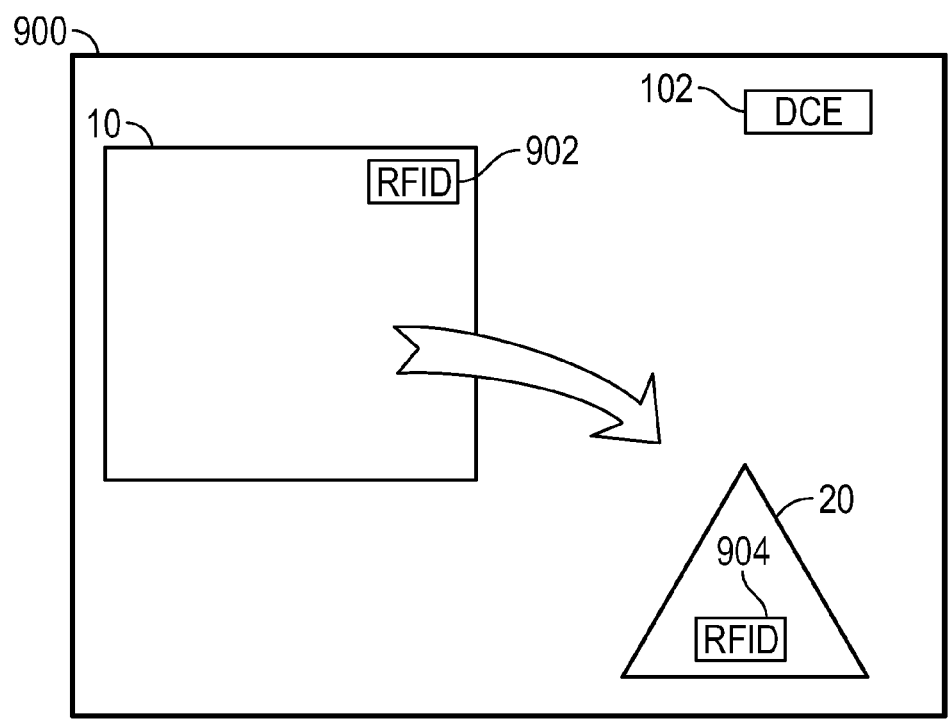
Figure 10:
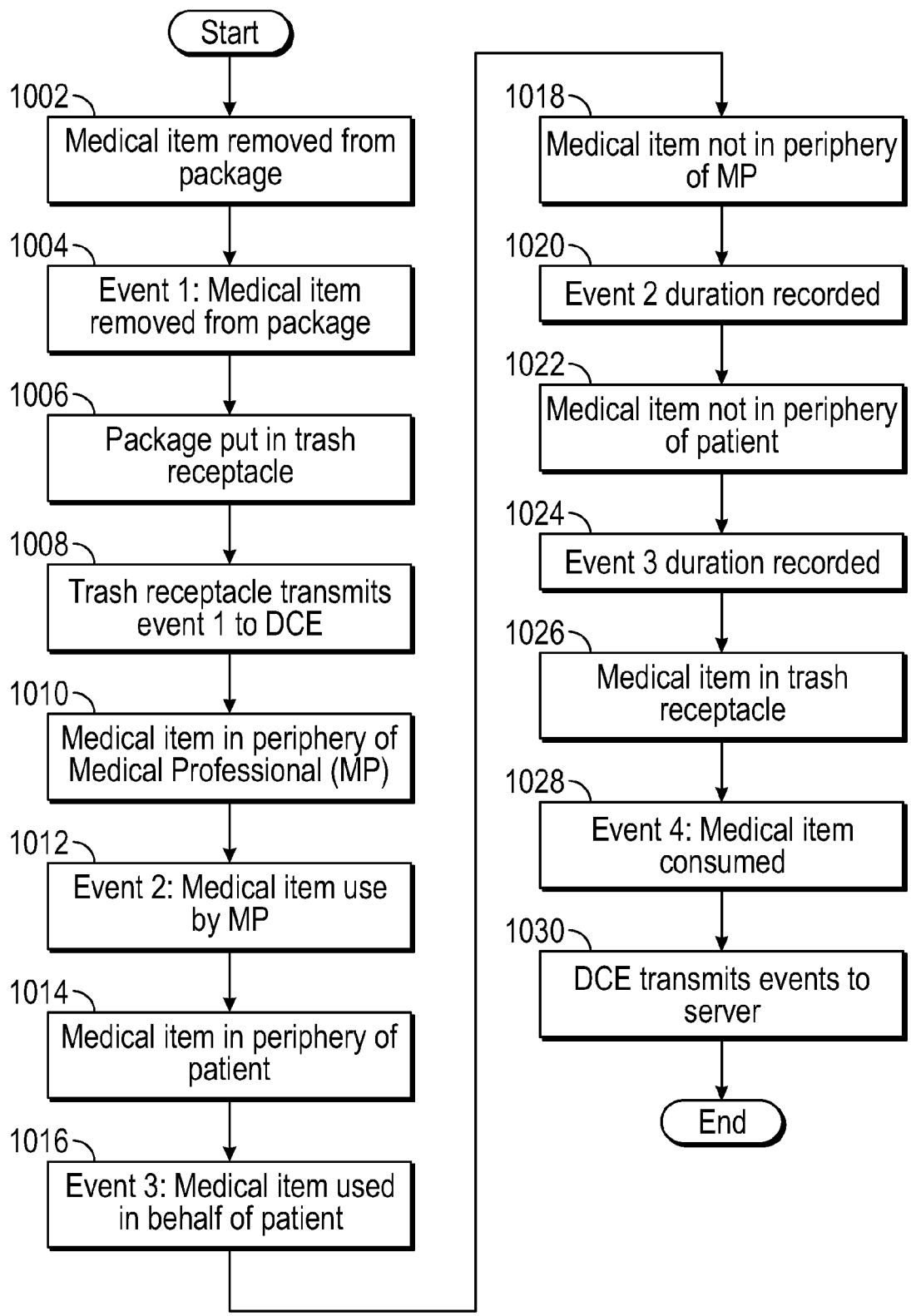
FIG. 10 is a flow diagram illustrating exemplary operations of the RFID chips in medical items and the DCE according to the exemplary operating environment shown in FIGS. 9A-9G.

At 1002, the medical consumable item 20 is removed from the package 10 as shown in FIG. 9B. At 1004, one or both of the RFID chips 902, 904 detects the separation and sends a message to the DCE 102 including a medical event indicative of the separation of the item 20 from the package 10.

Figure 9C:
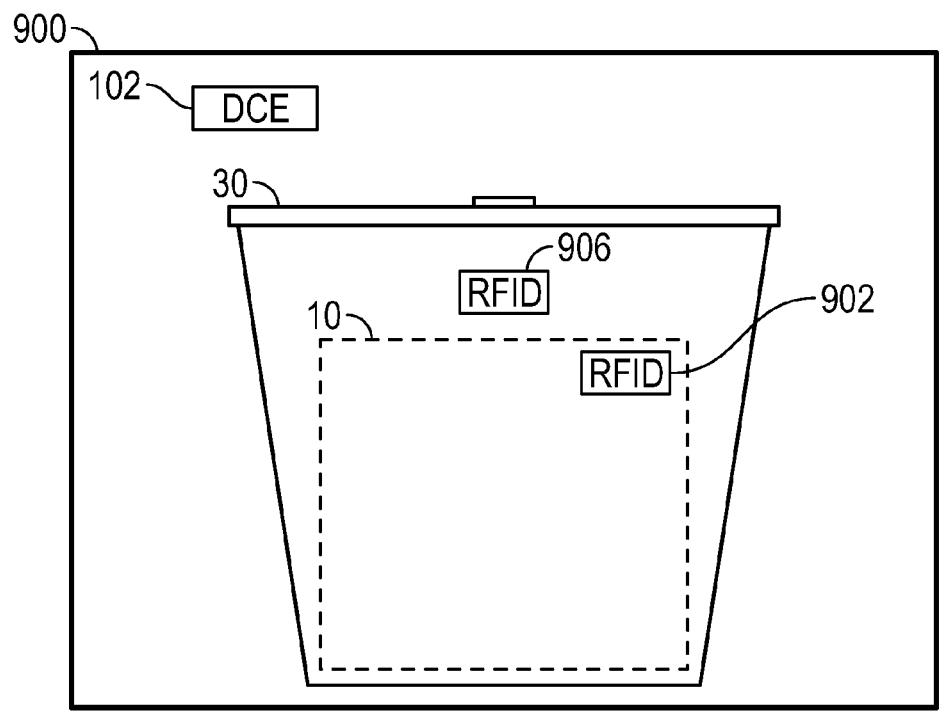

At 1006, the packaging 10 is placed in a trash receptacle 30 including a third RFID chip 906 as shown in FIG. 9C. At 1008, the third RFID chip 906 detects that the packaging 10 is in the receptacle 30 and sends a message to the DCE 102 including a medical event indicative of the packaging 10 being in the receptacle 30.

Figure 9D:
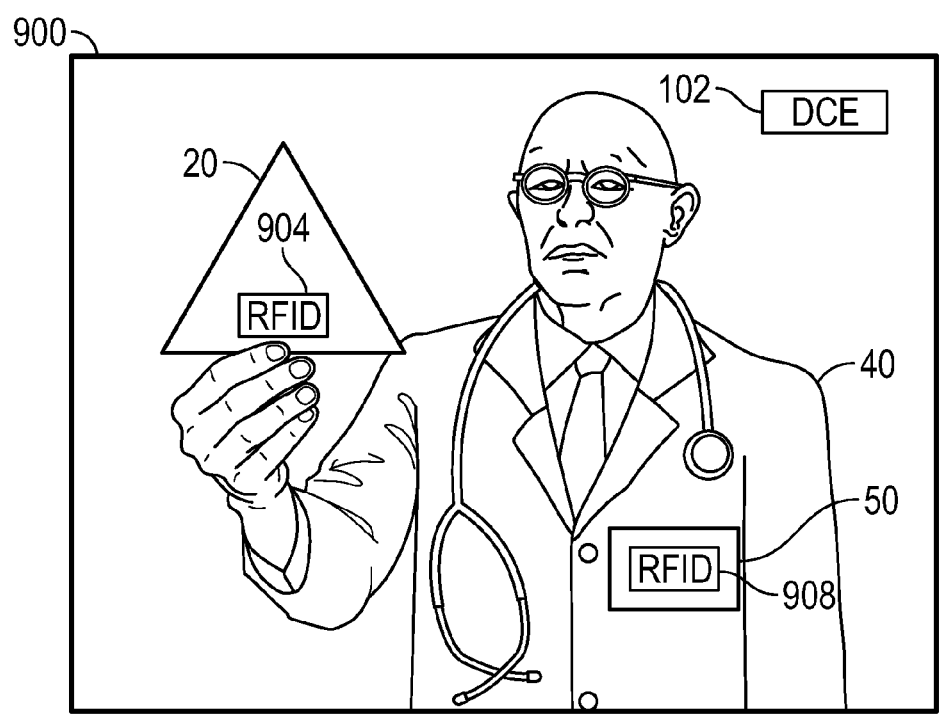

At 1010, a doctor 40 or other medical professional wearing a doctor identification or badge including a fourth RFID chip 908 has entered the room 900 as shown in FIG. 9D. The DCE 102 receives a registration message from the fourth RFID chip 908 when it enters the room. The doctor 40 holds the medical consumable item 20. At 1012, one or both of the RFID chips 904, 908 detects that the item 20 is less than a predetermined distance from the identification card 50, and sends a message to the DCE 102 including a medical event indicative of the item 20 being used by the doctor 50.

Figure 9E:
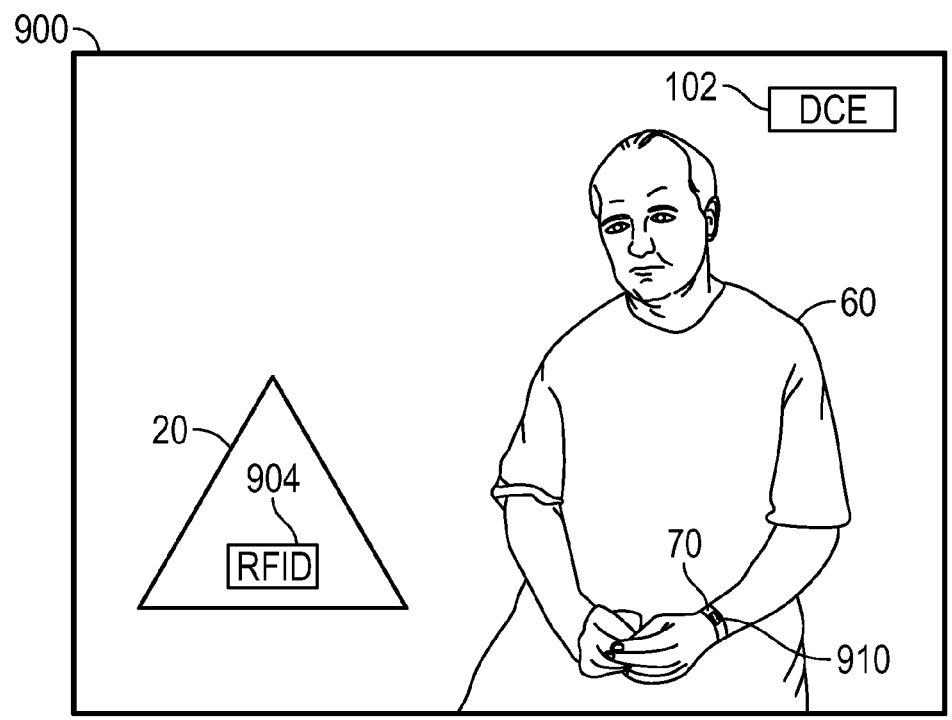

At 1014, a patient 60 wearing a patient identification or badge 70 including a fifth RFID chip 910 is in the room 900 as shown in FIG. 9E. The DCE 102 can receive a registration message from the fifth RFID chip 910 when it enters the room 900. The doctor, for example, holds the medical consumable item 20 near the patient 60. At 1016, one or both of the RFID chips 904, 910 detects that the item 20 is less than a predetermined distance from the patient identification card 70, and sends a message to the DCE 102 including a medical event indicative of the item 20 being used for the patient 60.

At 1018, when the medical professional 40 is more than a predetermined distance from the item 20 (or not within a periphery of near field detection), at 1020 one or both of the RFID chips 904, 908 detects that the item 20 is less than a predetermined distance from the medical professional identification card 50, and sends a message to the DCE 102 including a medical event indicative of the item 20 no longer being used by the medical professional 40 and the time duration for which the item was used.

At 1022, when the patient 60 is more than a predetermined distance from the item 20 (or not within a periphery of near field detection), at 1024 one or both of the RFID chips 904, 910 detects that the item 20 is less than a predetermined distance from the patient identification card 70, and sends a message to the DCE 102 including a medical event indicative of the item 20 no longer being used for the patient 60 and the time duration for which the item was used for the patient.

Figure 9F:
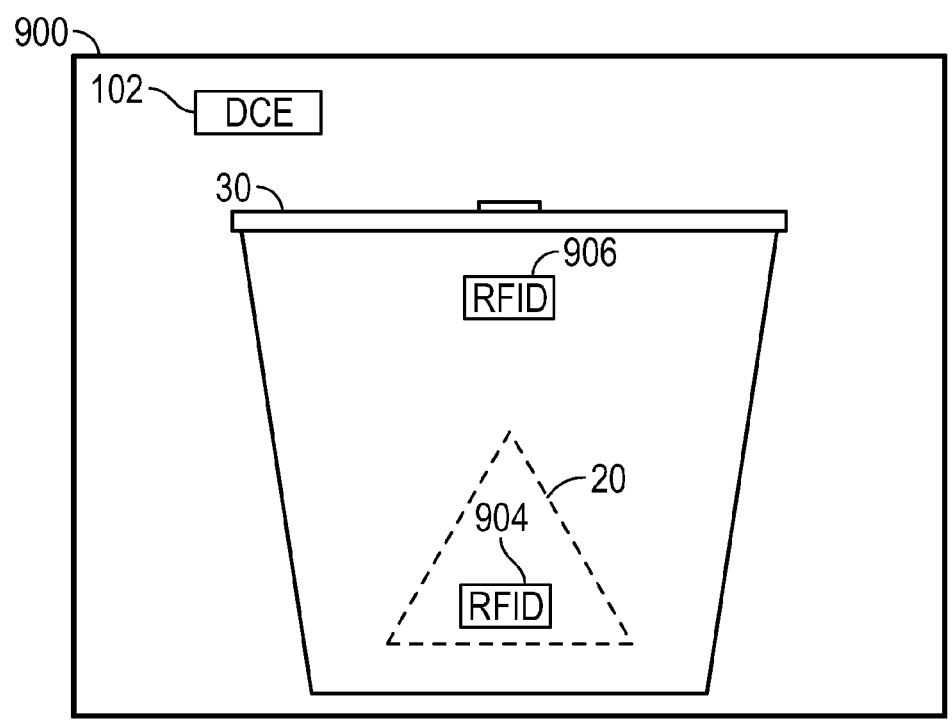

At 1026, the medical consumable item 20 is placed in a trash receptacle 30 including the third RFID chip 906 as shown in FIG. 9F. At this time, one or both of the RFID chips 904, 906 detects that the item 20 is in the receptacle 30 and sends a message to the DCE 102 including a medical event indicative of the item 20 being in the receptacle 30.

Referring to FIG. 9G, an exemplary conceptual message 920 generated by the DCE 120 (shown in human readable format) to be sent to the server is shown. The message 920 includes the series of events related to the medical consumable items discussed above. The time data can be determined by when the message from the RFID chip was received by the DCE or when it was sent to the server, or may be included in the message from the RFID chip. The location data can be generally the location of the DCE 120 and/or the RFID chip. The server device 1110 can store the data included in the message 920 in the database 1108 in the format depicted by 940. Particularly, information parameters can be stored according to an identification reference mapped to a given medical consumable item identity and/or any other entity identity referenced in a given message containing medical and/or situational data. Examples of such entity identity references include the actual product type or unique product identity associated with a given RFID chip identity, any medical professional (RFID chip identity associated with a medical professional) that may have been registered in proximity to an RFID chip with an identity that references a given item, any patient (RFID chip identity associated with a patient) that may have been registered in proximity to an RFID chip with an identity that references a given item, a room or trash receptacle referenced by a given DCE identity or RFID chip identity, etc.

The RFID chips can detect separation from another RFID chip or being within a predetermined distance from another RFID chip by the sensor group. Alternatively, the detection can be performed by ambient radio frequency communication techniques which can detect proximity up to, for example, 70 cm by backscattering. Further, the detection can be performed at the DCE end by, for example, measuring the RSS of the RF signal received from the chips.

The server device 1110 can determine what is represented by collective transactions based upon the medical data received from the DCE as well as previously stored medical data in the database 1108. For example, in a case the server device 1110 can determine that a series of events represent the following:

"Nurse Martin opened external ventricular drain sku #34567 on May 6, 2015 at 14:05 and the external ventricular drain packaging was placed in trash receptacle #56789 on May 6, 2015 at 14:05 in operating room number 1 at general hospital in Seattle, Wash."

"Nurse Martin gave external ventricular drain sku #34567 to Dr. Jones at May 6, 2015 at 14:06 in operating room number 1 at general hospital in Seattle, Wash."

"Dr. Jones inserted external ventricular drain into patient Ernie Smith on May 6, 2015 at 14:09 in operating room number 1 at general hospital in Seattle, Wash."

"Patient Ernie Smith left operating room number 1 at general hospital in Seattle, Wash. on May 6, 2015 at 14:52 and entered the post anesthesia care unit at general hospital in Seattle, Wash. on May 6, 2015 at 14:59 with external ventricular drain sku #34567"

"Patient Ernie Smith left the post anesthesia care unit at general hospital in Seattle, Wash. with external ventricular drain sku #34567 on May 6, 2015 at 15:23"

"Patient Ernie Smith arrived in the neurosurgical icu on ward 4G and was put in room 412 at general hospital in Seattle, Wash. on May 6, 2015 at 15:34 with external ventricular drain sku #34567 accompanied by nurse Washington."

"External ventricular drain sku #34567 was removed from patient Ernie Smith by Dr. Jones and placed in the trash receptacle in the neurosurgical icu on 4G at general hospital in Seattle, Wash. by nurse Williams on May 9, 2015 at 09:52."

The server device 1110 may publish (encrypted or unencrypted) messages, for example to a message queue or bus in response to certain events. External client devices or servers (subscribers) can register or subscribe to listen to particular messages or queues. When particular messages representing events of interest are received, the subscribing devices or servers, for example a particular hospital information system, can subsequently carry out downstream activities in response. For the sake of brevity the process of receiving a message from the message queue or bus is called herein notification. For example, an inventory system may be notified that an external ventricular drain was consumed, the electronic medical records system may be notified each day that the presence of an external ventricular drain with patient Ernie Smith is detected, the medical billing or hospital billing system may be notified that a consumable was used and that it should be charged to patient Ernie Smith, the providers billing system may be notified that Dr. Jones inserted an external ventricular drain catheter #34567 into patient Ernie Smith on May 6, 2015 and that he removed the catheter on May 9, 2015 in order to bill out these services, etc.

Second Embodiment

A second embodiment of the system will be discussed by exemplary cases in which parameters such as a position signature of one or more medical items is determined based upon medical data from the RFID chips.

Figure 12A:
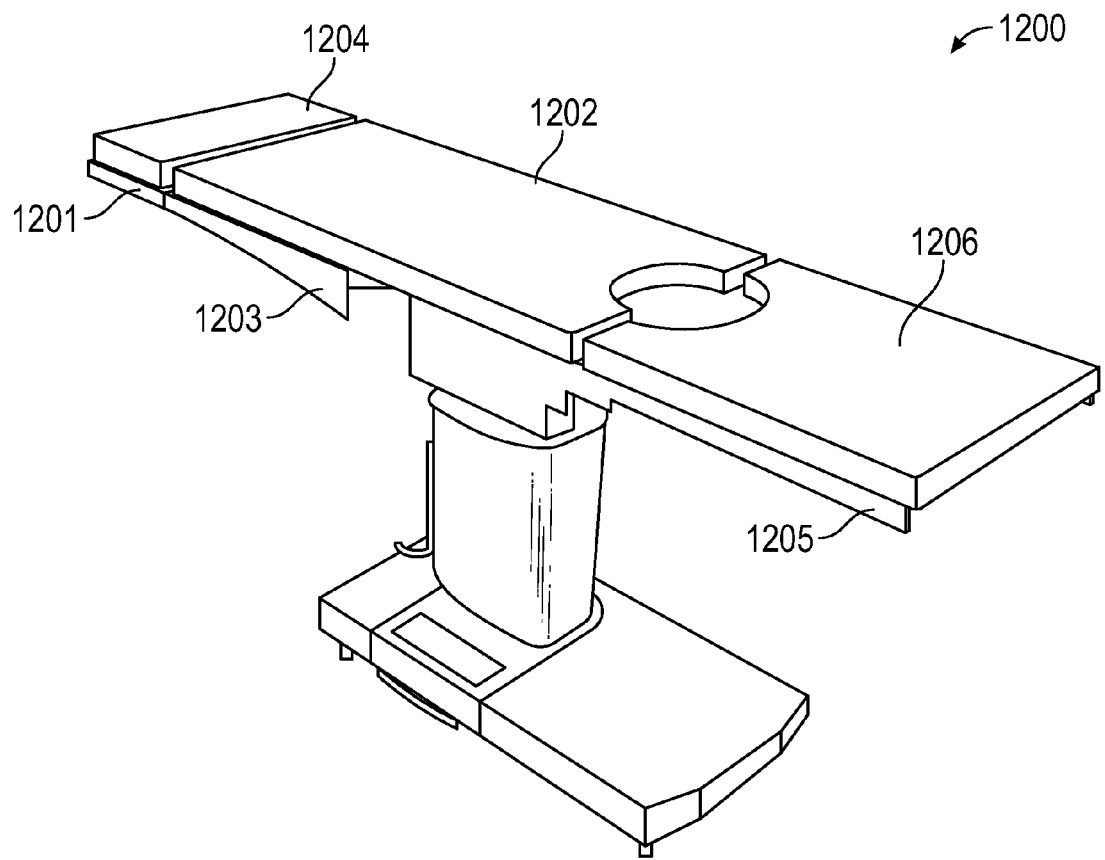
FIG. 12A is a perspective view of an operating table including a plurality of RFID chips according to an exemplary second embodiment.
Figure 12B:
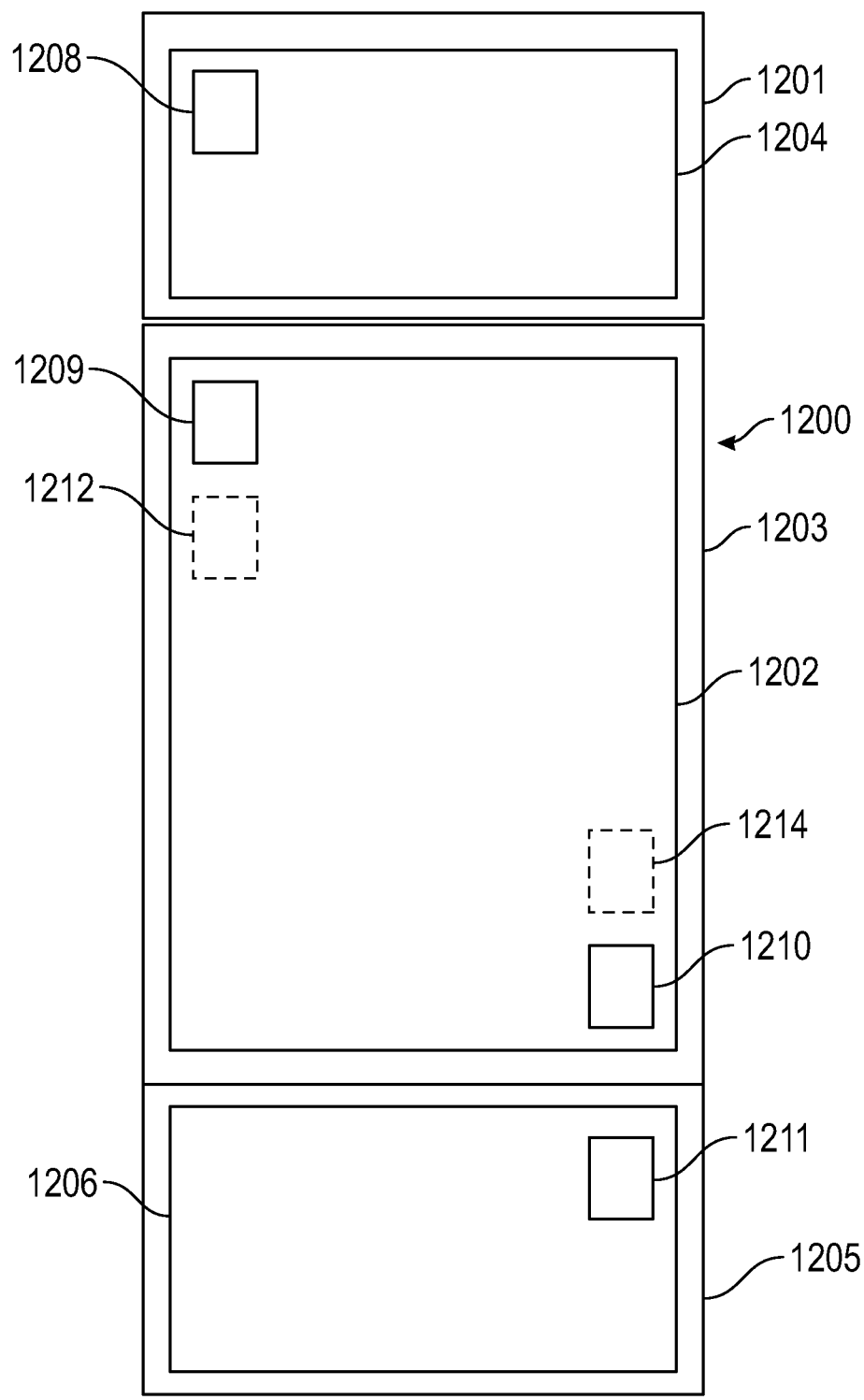
FIG. 12B is a diagram illustrating a top view of the operating table of FIG. 12A.

Referring to FIGS. 12A-12B, the medical item is a patient operating table 1200 and one or more of the RFID chips discussed above with respect to FIGS. 3A-3B are affixed to the table 1200. The operating table 1200 includes a foot cushion portion 1204 disposed on a foot portion frame 1201, a center cushion portion 1202 disposed on a center portion frame 1203, and a head cushion portion 1206 disposed on a head portion frame 1205. The foot cushion portion 1204 includes RFID chip 1208. The center cushion portion 1202 includes RFID chips 1209, 1210. The head cushion portion 1206 includes RFID chip 1211. The center portion frame 1203 includes RFID chips 1212, 1214. Preferably, at least one of the RFID chips 1209 and 1212 and the RFID chip 1210 and 1214 near edge of the center portion frame 1203 and cushion portion 1204 is an active-type RFID chip which includes or is electrically coupled to one or more or a network of pressure sensors.

Near field communication (NFC) between, for example, RFID chips 1209 and 1208, and between, for example, RFID chips 1210 and 1211 can be used to ascertain situational knowledge about the operating table configuration. Namely, whether the head of bed is connected (for example, whether the respective RFID chips are within a predetermined range of distance) to the center portion of the bed or not. Similarly, the presence or absence of the foot portion of the operating table can be determined from chips 1209 and 1208, for example. Information regarding the relative position and inter-chip distance between chips 1209 and 1212 and 1210 and 1214, for example, can be used to determine whether the cushion for the center portion of the operating table is in present and in place. Particularly, one or both of RFID chips 1209 and 1208 send registration data including the chip identification to the DCE, and sends a message including medical data indicating that it has established NFC with the other chip and the identification of the other chip. Similarly, one or both of RFID chips 1210 and 1211 send registration data including the chip identification to the DCE, and sends a message including medical data indicating that it has established NFC with the other chip and the identification of the other chip. The DCE sends messages including this medical data to the server device. The server device can determine whether the foot and head of bed sections are attached to the center portion of the operating table and from the identity of the chips and each chip's known reference to specific portions of the operating table, and which end is the foot of the bed based upon the medical data. Particularly, when both of RFID chips 1209 and 1208 have established NFC with each other, and both of RFID chips 1210 and 1211 have established NFC with each other, the location and relative positions of the head foot and center portions of the patient operating table 1200 can be determined.

Figure 13A:
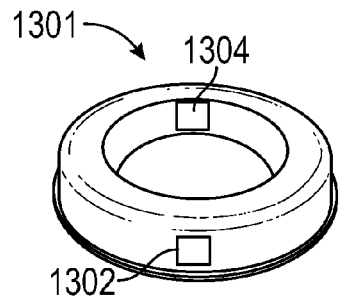
FIG. 13A is a perspective view of a donut headrest including a plurality of RFID chips according to the second embodiment.
Figure 13B:
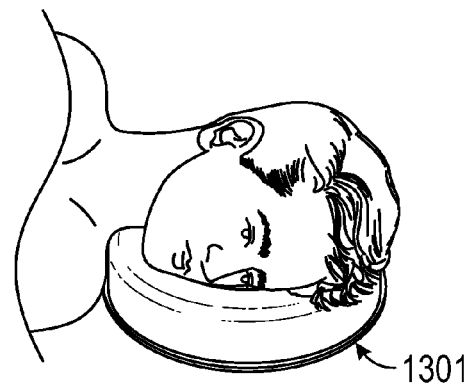
FIG. 13B is a schematic view of a patient's head positioned within the donut headrest of FIG. 13A.

Referring to FIGS. 13A-13B, a donut-type headrest 1301 (referred to here as donut) can be used on the patient operating table for patient head positioning. First and second RFID chips 1302 and 1304 affixed to the donut 1301 include pressure sensors and/or communicate with pressure sensors in the donut 1301. For example, imbedded just beneath the surface of the donut are a plurality of pressure sensors situated in a known configuration, at a known distance apart and in relation to each other to permit the measurement of the pressure, pressure gradient, and pressure distribution along the surface of the donut. A patient's head may be oriented in a large variety of ways on the donut 1301. Any particular position will result in a specific pressure distribution, herein called a position signature which can be detected by the RFID chips 1302 and 1304, and transmitted to the DCE along with a date and time stamp and other data collection related metadata. For example, as shown in FIG. 13B, the RFID chips 1302 and 1304 can detect the pressure distribution resulting from the weight of the patient's head and neck as transmitted to the donut at points of contact with the patient's neck, chin, ears, and any portion of the patient's face and scalp that come into contact with the donut. This data can be transmitted from the RFID chips 1302 and 1304 to the DCE along with a date and time and other data collection related metadata. The DCE or server device can determine the patient's head position based upon this data utilizing algorithms developed from machine learning techniques including neural networks, support vector machines, genetic programming/genetic algorithms, Bayesian statistics, decision trees, case based reasoning, information fuzzy networks, particle swarm optimization, simulated annealing, among others, that allow for complex pattern recognition, in some cases, leveraging pre-existing or previously collected "training" data, in addition to the newly acquired RFID chip data to predict an outcome, namely, in this example, the state or position of the patient's head, as will be discussed more fully below.

Figure 13C:
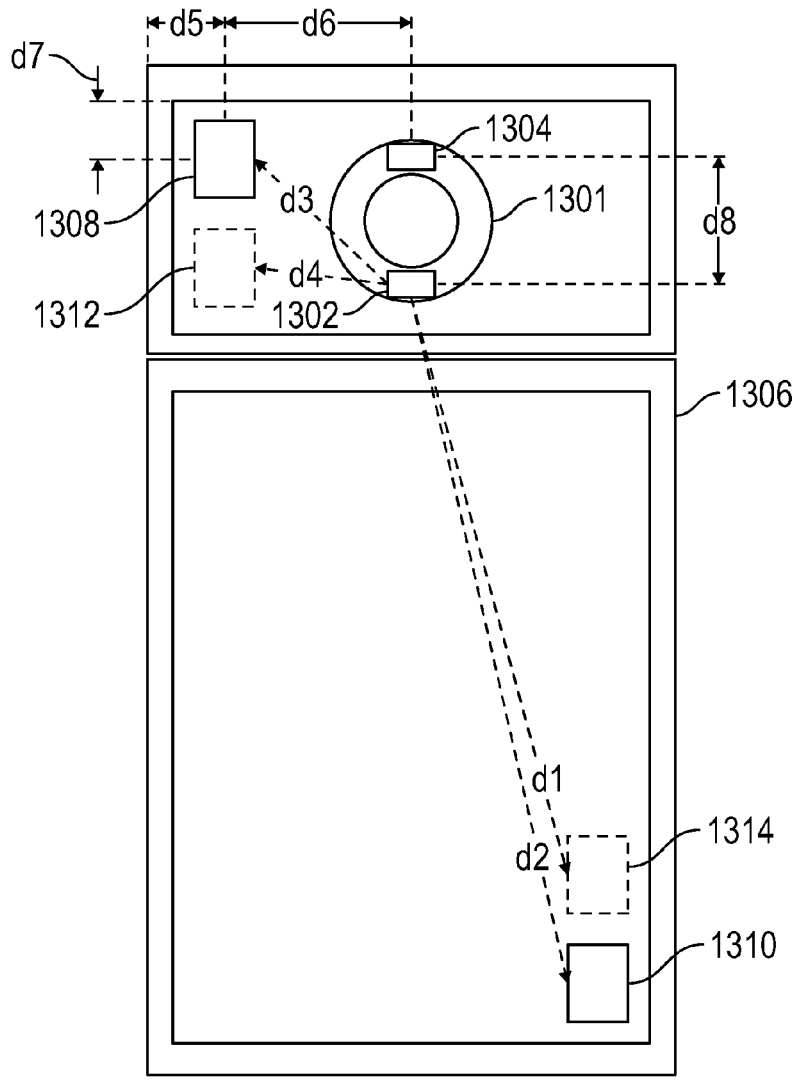
FIG. 13C is a diagram illustrating a top view of the operating table including the donut headrest according to the second embodiment.

Referring to FIG. 13C, the donut 1301 can be used together with the operating table 1306. The operating table 1306 includes first and second RFID chips 1308, 1310 on the cushion portion and RFID chips 1312, 1314 on the frame portion. When the donut 1301 is initially placed on the operating table, it is not known whether the donut 1301 is on the foot of the table or the head of the table. In the present embodiment, inter-RFID chip distances d1, d2, d3, d4, d5, d6, d7 and d8 are determined. For example, chips 1310, 1314 measure the distances d1, d2 to the chip 1302 on the donut 1301. RFID chips 1308, 1312 measure the distances d3, d4 to the chip 1302 on the donut 1301. Further, chip 1308 measures the distance d6 to tag 1304. Chip 1308 (or DCE) previously stores distances d5, d7. Further, chips 1302, 1304 can measure the distance d8 or the distance d8 can be previously stored. The distances can be measured by, for example, measuring an RSS of signals returned from other tags. Alternatively, one or more Sense-a-Tags (STs) can be included in the RFID tags or deployed separately. The inter-RFID distances are included in medical data sent from the RFID tags to the DCE, and are used to determine the relative positions of the donut 1301 and the table 1306, and thus where on the table 1306 the donut 1301 is located.

Figure 14A:
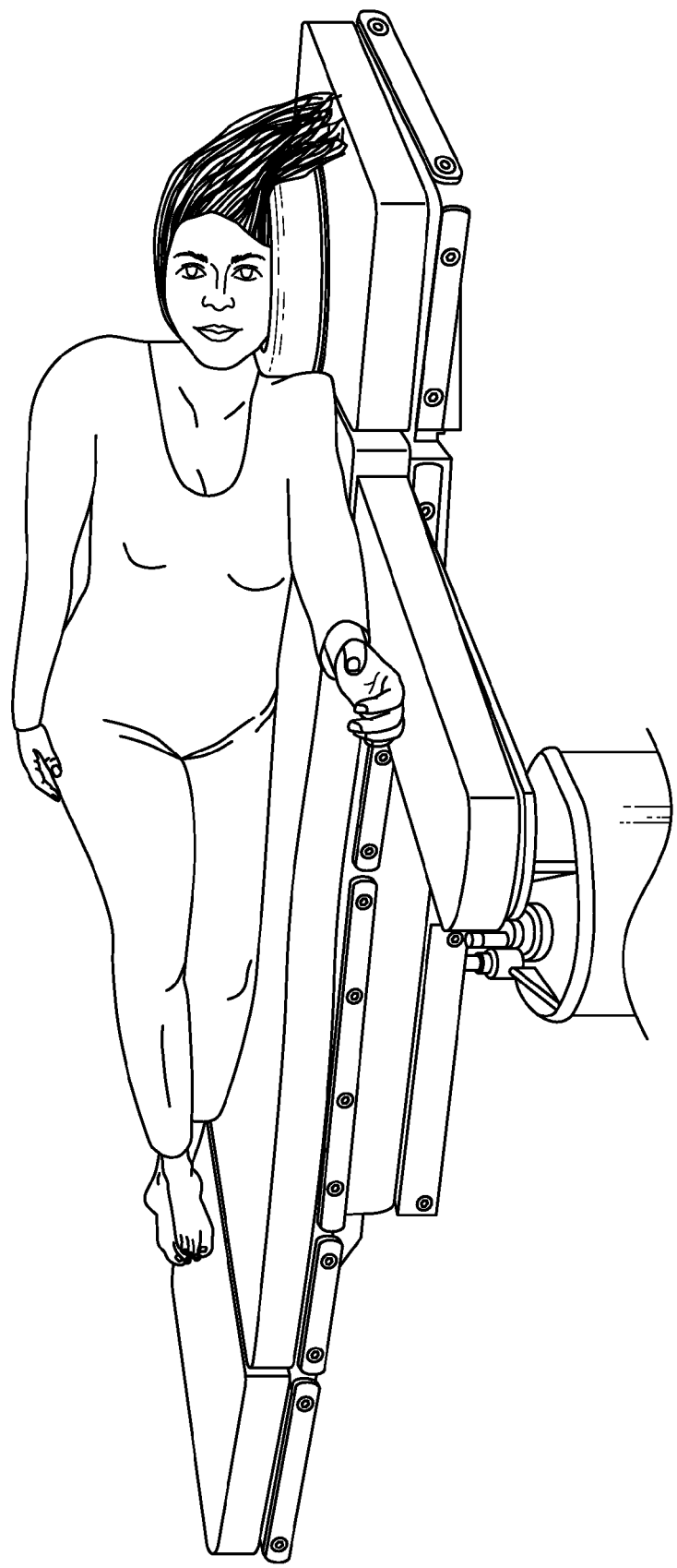
FIG. 14A is a perspective view of a patient positioned on her left shoulder on the operating table.
Figure 14B:
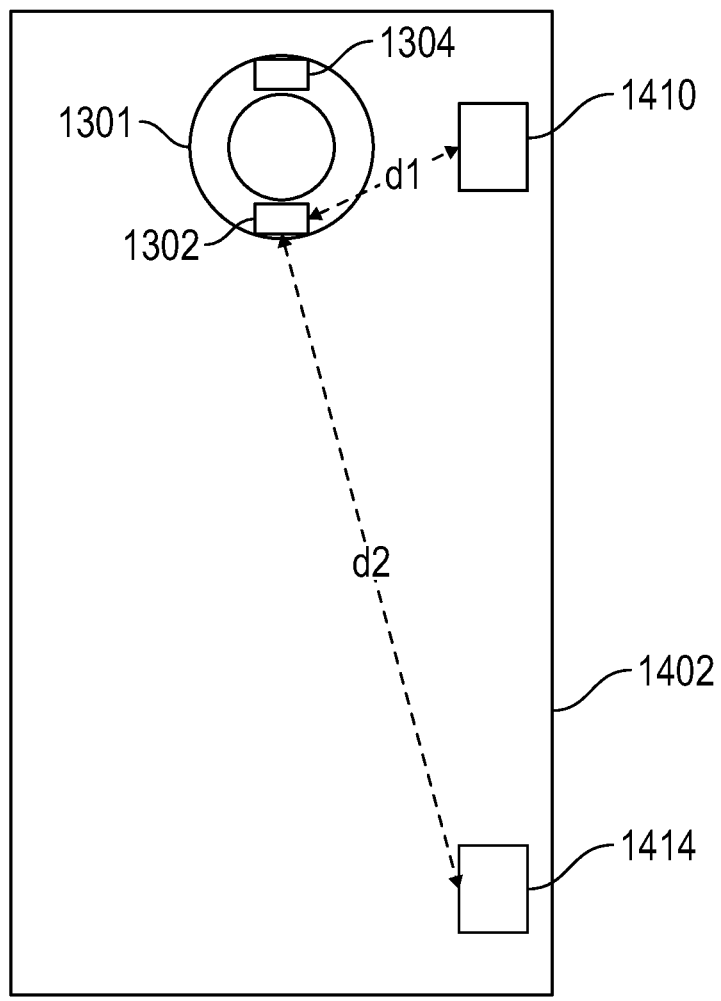
FIG. 14B is a block diagram illustrating the position signatures detected and communicated by the RFID chips on the donut headrest and the operating table according to the second embodiment.

Referring to FIG. 14A-14B, the data obtained from RFID chips on the operating table 1402 and the donut 1301 can be used to determine the position of the patient on the operating table 1402. FIG. 14B shows the data obtained from the RFID chips 1410, 1414 on the operating table 1402 (the patient's position signature) when the patient is positioned on the table as shown in FIG. 14A. The distance d1 between RFID chip 1410 and RFID chip 1302 (or RFID chip 1304) is shorter than the distance d2 between RFID chip 1414 and RFID chip 1302 (or RFID chip 1302). Thus, this data can be used to determine that the patient head location relative to the operating table. For example, if RFID chip 1410 is affixed to the frame or cushion of the head of the bed portion of the operating table, the information can be used to infer the patient's head is resting on the head portion of the operating table. However, if RFID chip 1410 is affixed to the frame or cushion of the foot portion of the operating table, the information can be used to infer that the patient's head is resting on the foot portion of the operating table, in a reverse orientation (relative to the names of the operating table foot and head portions). Further, RFID chips 1410, 1414 can detect pressure distribution of the patient's weight on the surface of the operating table and communicate this data or position signature along with a date and time stamp, and other data collection related metadata to the DCE. The pressure data can be used to determine, in this case, that the patient is on her left side. This pressure distribution data or position signature is obtained from pressure sensors within the operating table cushions or within a pad, for example a gel mat, placed on top of the operating table across one or more segments of the table. This network of a plurality of pressure sensors are situated in a known configuration at a known distance apart and in relation to one another and are employed to collect pressure distribution data which is then communicated to an imbedded or non-imbedded RFID chip either via wired connection or near field communication. The RFID chip(s) can be interrogated or can self-initiate communication with the DCE and communicate the RFID chip and pressure sensor pad identity along with the pressure data, location, and time of pressure data collection in addition to other data collection related meta data. Data can be collected at a variety of time intervals and be used to determine the change in the patient's position over time. For example, through the various phases of an operation, from the time the patient is first transferred to the operating, intubated, positioned for the procedure, extubated and transferred off of the operating table. The timestamps and position signatures obtained at different intervals can be used to determine, independently or in combination with other data, such as the type of case scheduled to be taking place in a particular location at a particular time to give one example, the phase of the operation that the patient is in at any given time and to predict the probability that the operation is or is not proceeding as intended, among other things. For example, if the patient's position at a particular phase of the operation is not as expected, such as the patient being positioned prone instead of supine as scheduled or on the left side instead of the right side as scheduled, etc. These predictions are made by the DCE or server utilizing algorithms derived from machine learning techniques discussed more fully below.

Figure 15A:
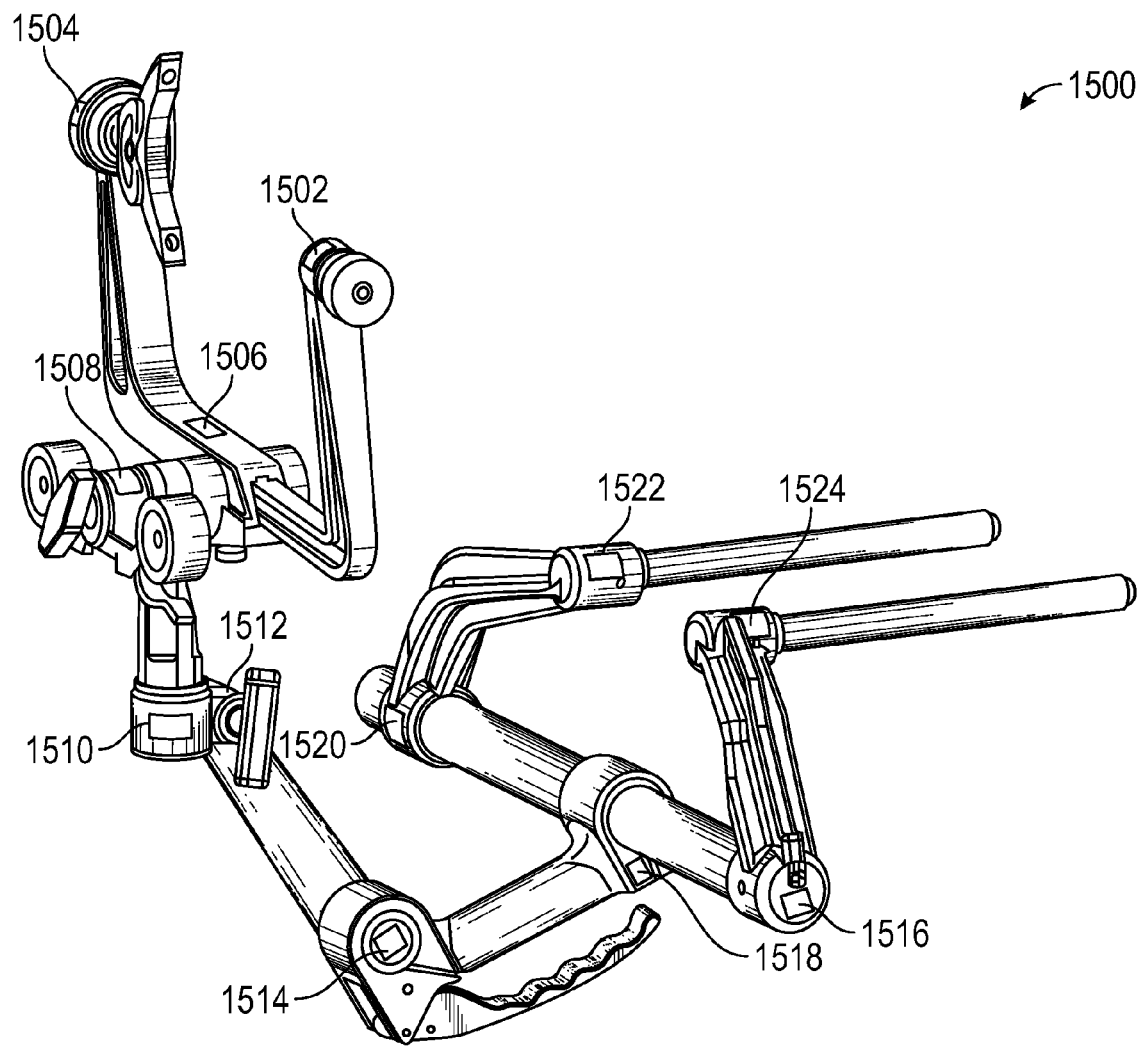
FIG. 15A is a diagram illustrating a skull clamp headrest including a plurality of RFID chips according to the second embodiment.
Figure 15B:
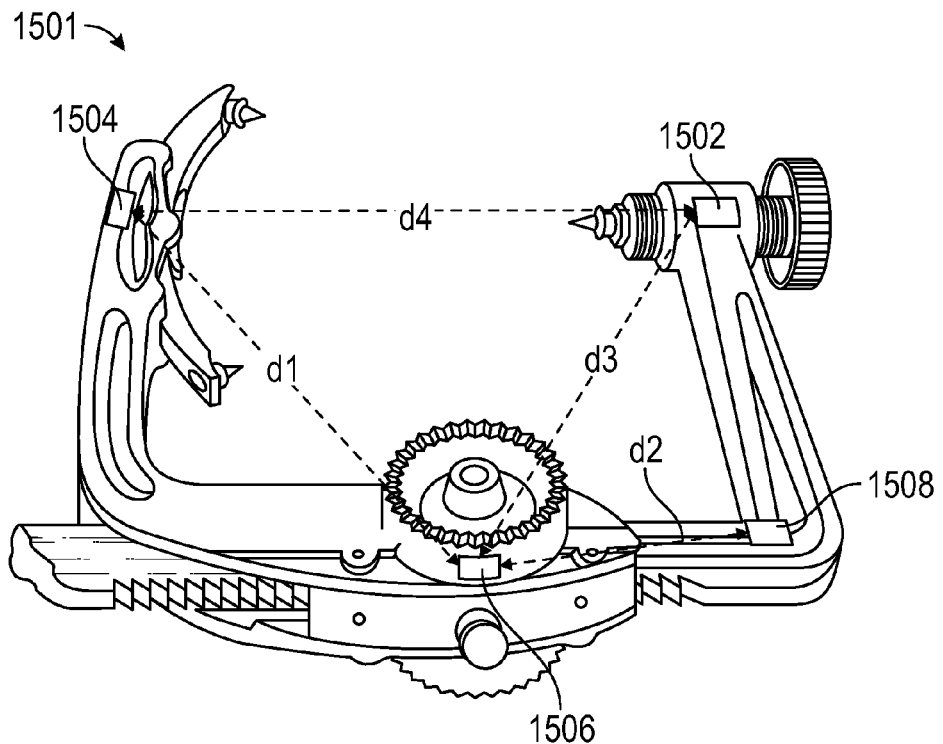
FIG. 15B is a diagram illustrating the skull clamp portion of the Mayfield headrest according to the second embodiment.

Referring to FIGS. 15A-15B, a skull clamp-type headrest 1500 can be used to position the patient's head in lieu of the donut discussed above. The head rest 1500 can be, for example, a Mayfield headrest, and includes a clamping portion 1501 which includes RFID chip 1504 near the two pin side and RFID chip 1502 near the one pin side of the clamp, an RFID tag 1506 near the base adjustment portion, and an RFID tag 1508 in a corner portion. As shown in FIG. 15A, a swivel portion is joined to the clamping portion 1501. The swivel portion may be similar to the swivel adaptor and base unit described in U.S. Patent Publication No. 2006/0190010 to Easton published on Aug. 24, 2006, the contents of which are incorporated herein by reference. A plurality of RFID chips 1510, 1512, 1514, 1516, 1518, 1520, 1522, 1524 can be disposed on the pivot/swivel joints of the swivel portion of the head rest 1500.

The respective orientations of the RFID chips in the headrest 1500 can be used to determine the exact spatial orientation of the support arm and clamping portion. For example, the RFID chip 1506 near the adjustment portion can measure a vector including an orientation angle and displacement of the chips 1502, 1504, 1506, 1508 from a base line orientation. The vector can be represented as [θ, d1, d2, d3], wherein θ represents the angle from the baseline orientation, d1 represents the distance between chips 1506 and 1504, d2 represents a distance between chips 1506 and 1508, and d3 represents a distance between chips 1506 and 1502. The RFID chip 1504 can measure a distance d4 from chip 1502 (or vice versa). The RFID chip 1506 can send a message to the DCE including the vector and the distance d4 (received from one of chips 1502, 1504), the various RFID chip identities, date and time stamp of the data collection, and other data collection related metadata. The DCE can send this message to the server device. The server device can utilize machine learning techniques described herein to predict or determine the position of the headrest and thus the position of the patient's head based upon the vector and d4.

Referring to FIGS. 15C-15F, exemplary operations of the headrest 1500, the DCE and the server will be discussed during two exemplary patient positions. In these examples, a baseline orientation is determined to be as shown in FIG. 15B. That is, the angle θ of the baseline orientation is 0 degrees. The RFID chip 1506 is an active-type RFID tag, and RFID chips 1504, 1506 and 1508 are passive-type chips.

Figure 15C:
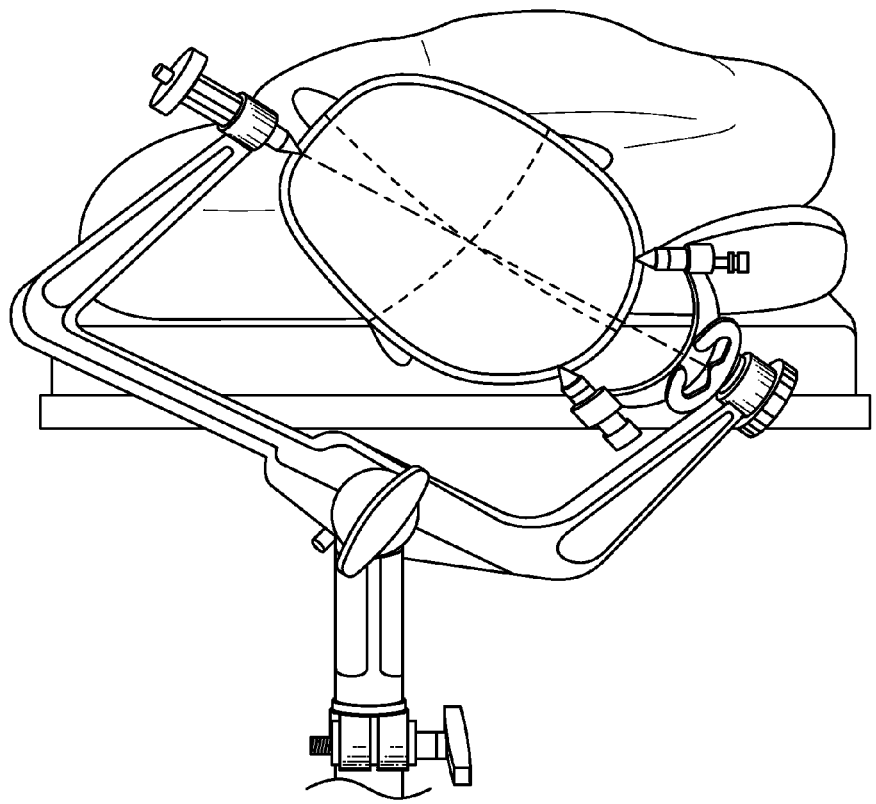
FIGS. 15C-15F are diagrams illustrating various orientations of a patient's head positioned in the skull clamp and the detected position signatures.

In FIG. 15C, a patient's head is shown positioned within the clamp 1501 while the patient is in the supine position. Prior to, or at this time, the RFID chip 1506 sends a registration message to the DCE including its identification information, data collection date and time stamp information, and other data collection related metadata. Further, passive-type RFID chips 1504, 1506 and 1508 receive power wirelessly from either the DCE or the RFID chip 1506, and send registration messages to the DCE including their identification information, registration date and time stamp information, and other related data collection metadata.

Figure 15D:
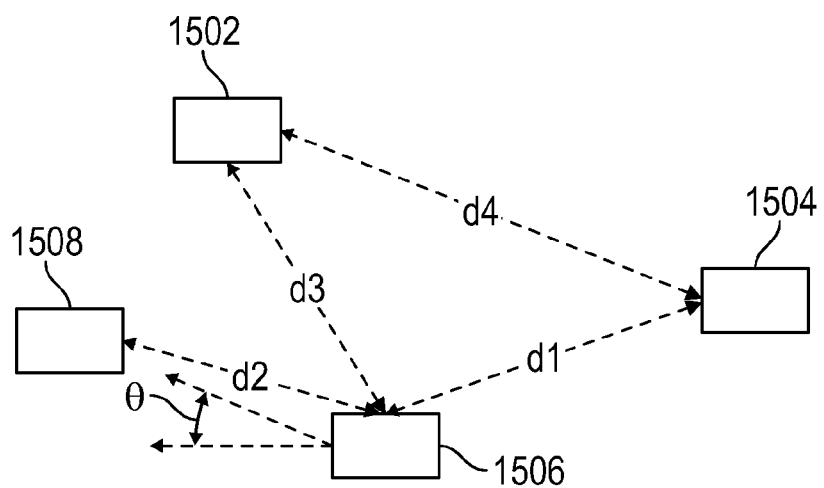

As shown in FIG. 15D, the RFID chip 1506 detects its displacement angle θ from the baseline orientation. For example, the sensor group of the RFID chip 1506 may include an accelerometer or orientation sensor for measuring the displacement angle. The RFID chip 1506 also measures the distances d1, d2, d3 to each of the RFID chips 1504, 1506 and 1508. The distance can be obtaining by measuring the RSS of a received signal from the chips or by NFC. Further, the RFID chip 1506 receives from one or both of RFID tags 1502, 1506 the distance d4 between RFID chips 1502 and 1504. The RFID chip 1506 send another message including the position vector [θ, d1, d2, d3] and also the distance value d4 to the DCE. The value of θ is greater than 0 and may be, for example, 30 degrees. The values d2, d3, d4 are greater than their baseline values. The value d1 will generally be fixed and can be used for error correction.

Figure 15E:
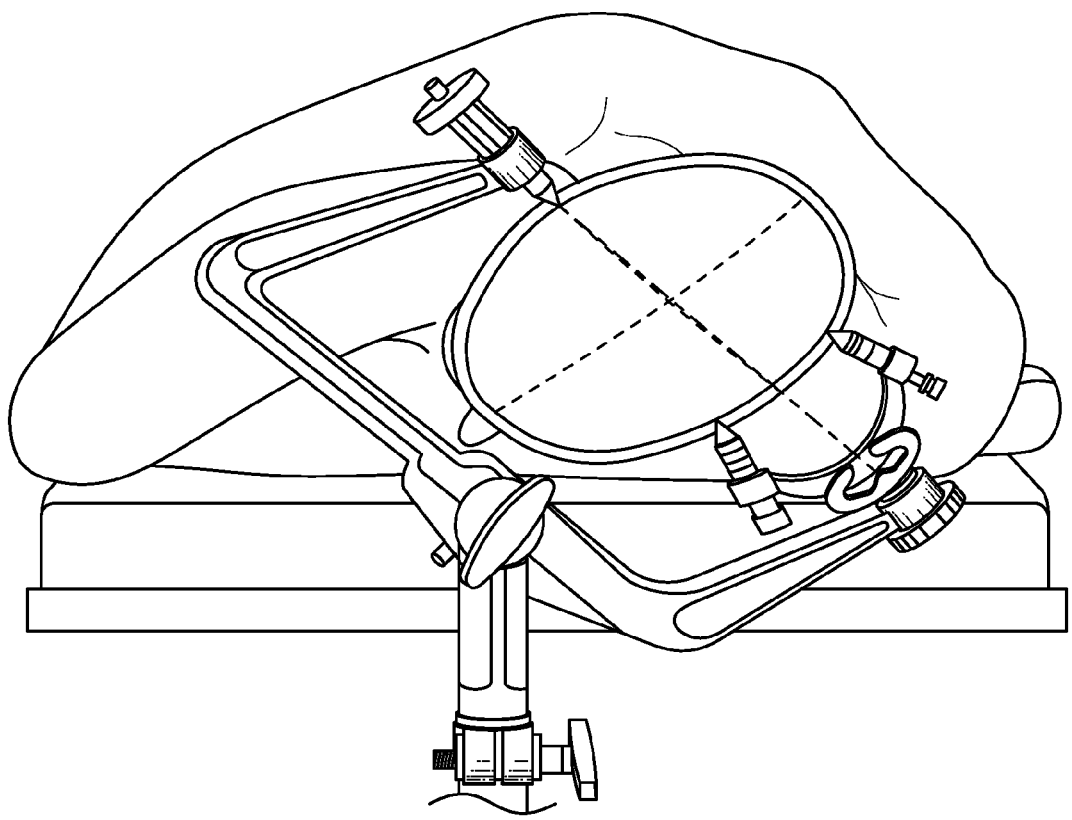
Figure 15F:
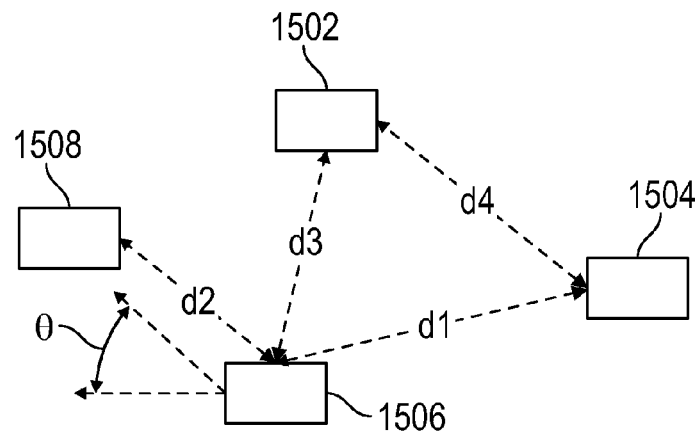

In FIG. 15E, a patient's head is shown positioned within the clamp 1501 while the patient is in the lateral oblique position. If not registered, the RFID chip 1506 sends a registration message to the DCE including its identification information. Then, the RFID chip 1506 obtains the position vector [θ, d1, d2, d3] and the distance value d4 and transmits this data in a message to the DCE as discussed above. The value of θ may be, for example, 45 degrees. The values d2, d3, d4 are greater than their baseline values, but less than the values of the case shown in FIG. 15C. The relative distance between the RFID chips on the head clamp 1501, the support arm as shown in 1500, and the RFID chips affixed to the various portions of the operating table as in the exemplary FIGS. 12C and 13C will also be transmitted to allow the determination of the location of the head clamp to the operating table (for example, is it affixed to the head or the foot of the operating table, etc.).

As discussed in embodiment 1, the patient can have a patient identification such as a wristband which includes an RFID chip that stores the patient identification. This information will also be transmitted to the DCE as discussed in embodiment 1. Similarly, the identification of the medical professional will also be transmitted to the DCE as discussed in embodiment 1. The DCE will send this information to the server device.

The server device can determine, utilizing machine learning algorithms as described herein, the patient position based upon the position signature received from the RFID chip 1506. For example, when the server receives the message including the position vector [θ, d1, d2, d3] and the distance value d4 shown in FIG. 15C, it can determine that the patient's head is rotated as shown in FIG. 15C when the values of the position vector are within a first predetermined range. When the server receives the message including the position vector [θ, d1, d2, d3] and the distance value d4 shown in FIG. 15E, it can determine that the patient's head is rotated as shown in FIG. 15D when the values of the position vector are within a second predetermined range different from the first range. Moreover, this data can be combined with the medical data received from the operating table as shown in FIG. 14B to increase the accuracy of the determination.

The server device can then compare the patient's position with patient attributes stored in the database to determine if a never event has or is about to occur. For example, if a patient attribute in the database indicates that the patient is scheduled to have a surgical procedure on a left portion of his head, yet the server determines that the head is positioned to expose the right portion as shown in FIG. 15C, the server device determines to a certain probability that a never event has or is about to occur. Similarly, the server device can compare the identification of the medical professional with the scheduled surgical procedure to confirm if a never event has or is about to occur. For example, if a medical professional is scheduled to do a surgical procedure on a patient different from the patient identification in the message received from the DCE, the server device can determine that a never event has or is about to occur. Further, if the server device determines that a medical consumable item such as a sponge with an imbedded RFID device is still in the patient as determined from the consumable's (sponge's) proximity to one or more of the RFID chips, for example, those affixed to the operating table and or the donut or head clamp at the time of completion of the surgery, the server device may determine that a never event has or is about to occur.

Figure 16A:
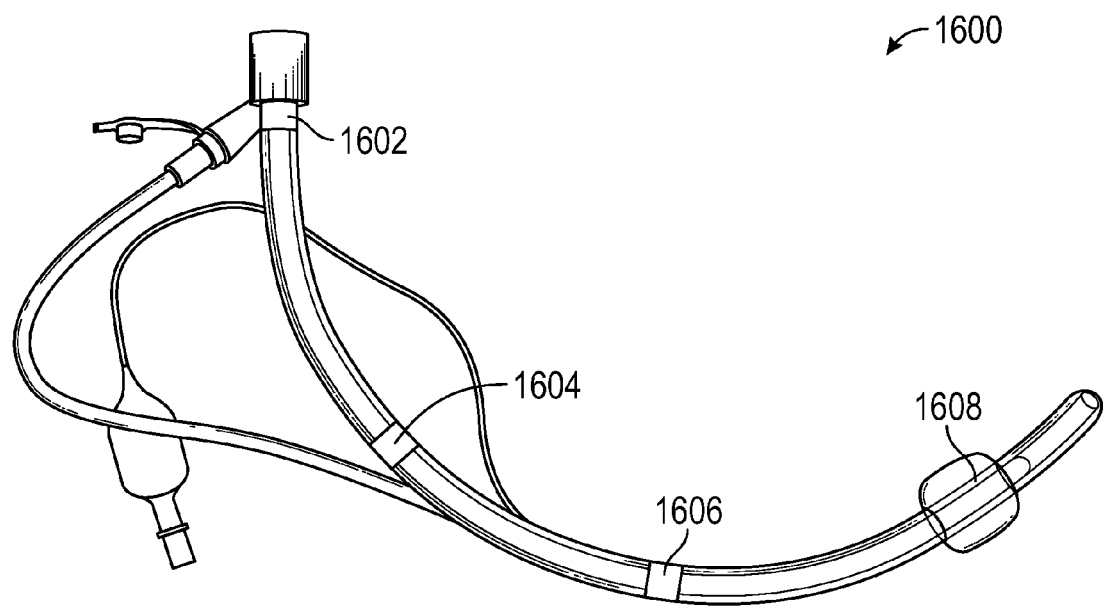
FIG. 16A is a diagram illustrating an endotracheal tube including a plurality of RFID chips according to the second embodiment.
Figure 16B:
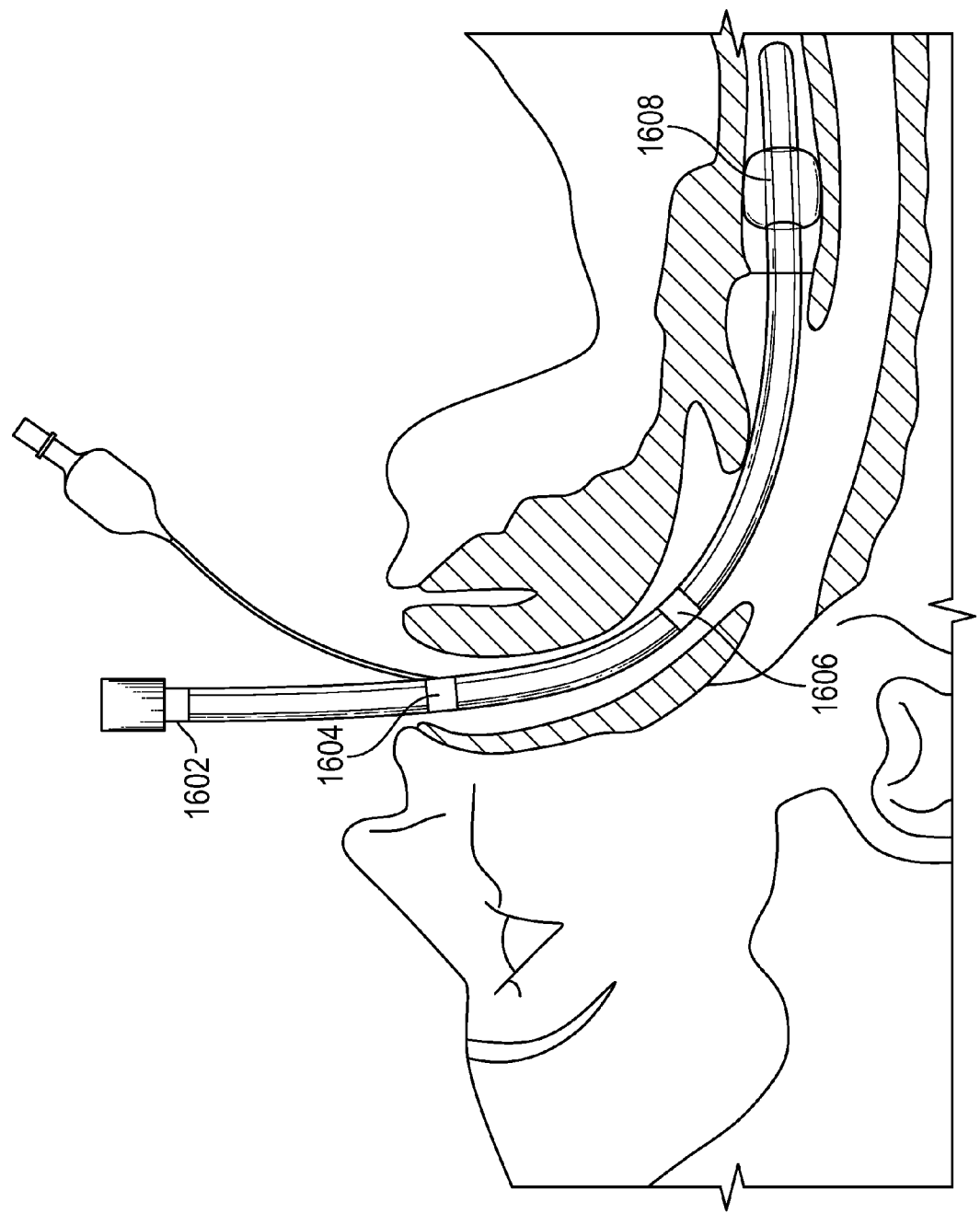
FIG. 16B is a view of the endotracheal tube positioning within a patient.

Referring to FIGS. 16A-16B, an indwelling catheter such as an endotracheal tube 1600 includes first RFID tag 1602, second RFID tag 1604, third RFID tag 1606, and fourth RFID tag 1608 on the air-filled cuff of the tube 1600. At least fourth RFID tag 1608 includes or is associated with pressure, orientation and temperature sensors. The first RFID tag 1602, second RFID tag 1604, and third RFID tag 1606 include or are associated with temperature, pressure and orientation sensors. The pressure sensors are disposed in an orientation where they can enable the detection and monitoring of the pressure of the cuff of the endotracheal tube at the interface between the cuff and the patient's airway. The temperature sensors are located along the long axis of the endotracheal tube and have a known position or measured distance from the end of the endotracheal tube. As shown in FIG. 16B, the first RFID tag 1602 and second RFID tag 1604 can preferably be positioned so as to be exterior and near the patient's mouth, while third RFID tag 1606 and fourth RFID tag 1608 are positioned to be in the patient. The tags can transmit data to the DCE representative of cuff inflation changes (pressure), the temperature distribution along the endotracheal tube, and the patient's core body temperature over time. The distribution of temperature along the course of the endotracheal tube at any particular moment in time used in combination with the known position of each temperature sensor within the endotracheal tube is transmitted to the DCE by the associated RFID chip. The DCE or server can then determine, using the machine learning techniques, the likely position of the endotracheal tube leveraging the knowledge of the expected temperature drop off along the course of the endotracheal tube as it move from the trachea to the larynx to the pharynx to where it exits the patient at which point it then gets exposed to the ambient temperature in the operating room. In addition to using this temperature distribution to predict the position of the endotracheal tube in the patient at any given moment in time, changes in the temperature distribution along the course of the endotracheal tube over time can be used to determine whether the endotracheal tube has moved in the patient which can be useful, for example if the system predicts that the endotracheal tube is no longer in ideal position or is potentially at risk of becoming dislodged or conversely if the tube may potentially become positioned too deep in the patient's airway. The cuff pressure at any particular point in time or changes in the cuff pressure over time can also be used to predict situations that may pose danger or risk to the patient.

The temperature and pressure distribution can be used to determine if the catheter poses a risk to the patient. Particularly, the sensors can measure a temperature and pressure at most distal aspect of the catheter and a temperature and pressure gradient along the long axis of the catheter. The temperature and pressure data can be used to determine (1) when the catheter was introduced (inserted) (2) when the catheter was discontinued (removed) (3) the location of the air-body interface (point along the catheter where it exits the surface of the human body) as determined from the temperature gradient along the long axis of the catheter. A trained Neural Network Model (NNM) can be used to predict 1) when a catheter is at risk of falling out based on depth or change in depth over time; and 2) when a catheter may be putting a patient at risk (i.e. catheter days which can be a risk factor for development of infection) based on, for example, i) date of placement comparison with current date; and ii) lessons learned (outcomes of clinical interest) from data collected from other patients with similar catheters (supervised learning).

MLA can be used to train the NNM based upon a catheter risk state event such as cases of known catheter discontinuance cases (removal or inadvertent discontinuation) and the temperature or pressure gradient and change thereof over time along the long axis of the catheter for each case. Thus, machine learning can use the data therein derived from temperature or pressure sensors over time and learn on an ongoing basis what pattern of change in the temperature gradient denotes risk of or actual discontinuance be it intentional or incidental.

MLA can be used to train the NNM based upon a catheter risk state event such as cases of catheter related infections and event metadata thereof (from hospital information systems—i.e. blood cultures, urine cultures, sputum cultures, white blood cell count, vital signs such as temperature curve, coding/claims data, etc.) as well as the temperature data from catheter temperature sensors to learn what patterns in the event metadata/catheter introduction denote developing risk of a catheter related infection.

Referring to FIG. 17, an exemplary case is shown in which the Mayfield headrest 1500 can be used in place of the foot frame and foot cushion of the operating table (as is typical in neurosurgical procedures) 1202 and the endotracheal tube 1600 is inserted in the patient. The data from all of the RFID chips can be sent to the DCE, and used to determine the position of the patient and whether a never event has or is about to occur. Position data from the RFID chips on the endotracheal tube 1600 relative to the position data from the RFID chips on the operating table 1202 and the position data from the RFID chips on the Mayfield head clamp 1501 can be used together to improve the prediction of the patient's head orientation. For example, if RFID chip 1602 is closer in proximity to RFID chip 1502 as compared to its distance from RFID chip 1504 (as would be the case in the exemplary case shown in FIG. 17), this information can be used by the system to determine or further confirm the orientation of the patient's head in the head clamp. Specifically, the combined information from RFID chips on the head rest and those imbedded in the endotracheal tube enable more specific determination of where the patient's face or the frontal bone of the skull is relative to the head clamp as opposed to the patient's occiput or the occipital bone of the skull (back of the head).

Referring to FIG. 18, an eyelid occlusive dressing 1800 includes an embedded RFID tag 1802. Eye protection is used by anesthesiologists during neurosurgical cases to prevent eye injury (i.e. corneal abrasions, chemical injury from prep solutions, exposure keratopathy/keratitis). The eyelid dressing's embedded RFID tag 1802 can transmit orientation data to the DCE that can be used together with the orientation data from the Mayfield head rest 1500 and the head clamp 1501 to determine the orientation of the patient's head by, for example, calculating the proximity of the RFID tag 1802 to those on the Mayfield head clamp 1500 and 1501.

Referring to FIG. 19, rather than the donut 1300 shown earlier in FIGS. 13A-13B, the head rest can be a horse shoe style headrest 1900 which includes RFID tags 1902, 1904 and 1906. Further, the headrest 1900 can be installed on its own swivel joint. For example, a horse shoe shaped head rest can be affixed to the Mayfield apparatus rather than the head clamp 1501.

This information along with similar information about the proximity of the endotracheal tube 1600 to the RFID chips on the Mayfield head rest 1500 enhance the ability of the server and/or DCE to definitively determine the orientation of the patient's head and to predict the side of the patient's head that will be operated upon, which the system can cross reference with the booking information for the case to determine if all information is in agreement or whether there may be risk for a never event.

It should be noted that in FIG. 1, one server was shown merely for ease of illustration. However, the server 114 may be a plurality of servers and databases connected to the network 112 via a load balancer and performing X, Y and Z axis scaling of the hardware and software. Particularly, multiple virtual machine instances (VMs) can be running applications behind the load balancer on the different servers (X-axis), the servers can perform a functional decomposition to break up applications into small services (Y-axis), and each server (running the identical application) can be responsible for a subset of the data (sharing the database) broken up by something that logically makes sense for the business (i.e. patient last name, type of customer, etc.) with a component for routing (Z-axis). Further, although the database 1108 in FIG. 11 is shown as being a portion of the server 1110, it should be noted that the database 1108 can be implemented at one or more separate computing devices connected to the server 1110 via the network.

ALTERNATIVE EMBODIMENTS

In alternative embodiments of the system, the medical item can refer to medical storage units and instruments or items stored in the storage units similarly to as shown in FIG. 9A. Each of the medical storage units include RFID tags and/or a DCE and some or all of the instruments in the medical storage unit include RFID tags. The RFID tags communicate messages including medical data to the DCE and therefore the server similarly to as shown in FIG. 1. The server can store this information in the database to determine events or monitor usage patterns of the medical item(s). Further, the server can determine an event based upon input attributes included in the medical data using a trained model.

Figure 20A:
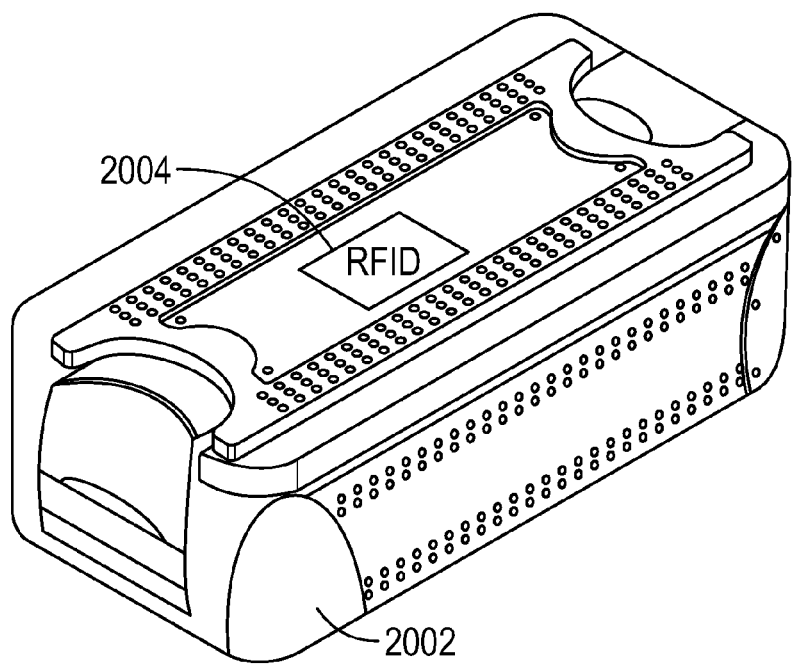
FIG. 20A is a diagram illustrating a sterilization case including an RFID chip.
Figure 21:
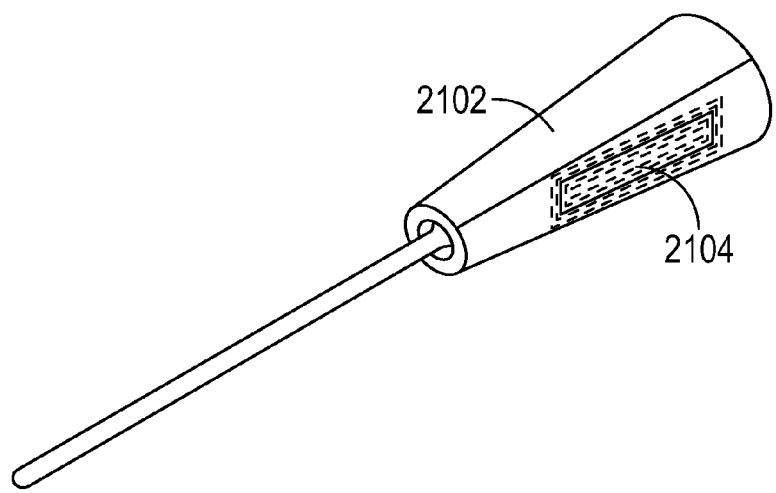
FIG. 21 is a perspective view illustrating a medical instrument with an RFID tag located on an outer surface of the instrument.
Figure 27:
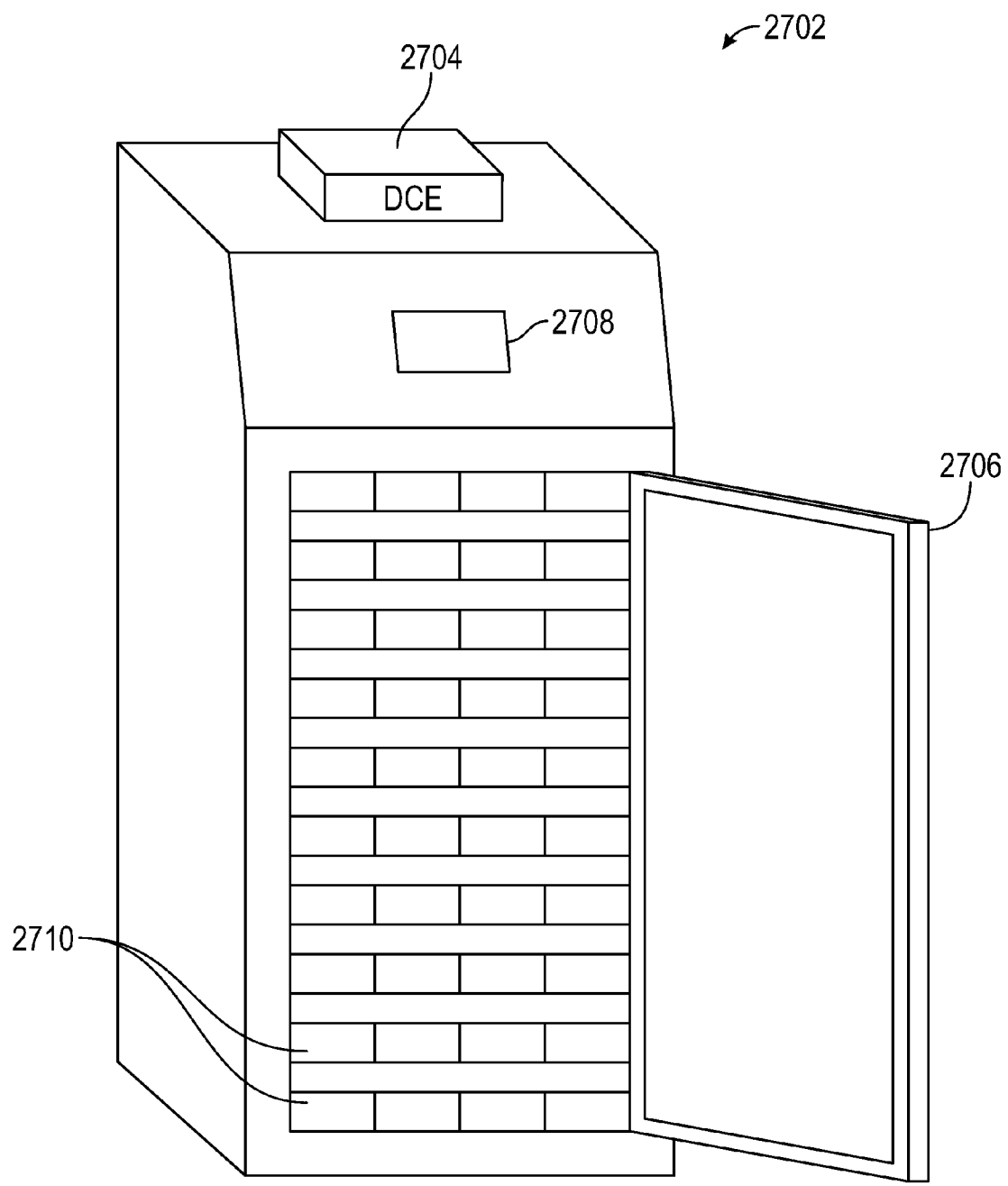
FIG. 27 is a diagram illustrating an exemplary climate controlled tissue storage cabinet.

Referring to FIG. 20A, the medical item can be an instrument tray case 2002 containing various medical instruments such as, for example, medical instrument 2102 shown in FIG. 21. The case 2002 includes an RFID tag 2004. The RFID tag 2004 may be an autoclavable RFID tag which can withstand the extreme temperature swings (cold or heat) and pressure of an autoclave machine (such as shown in FIG. 27). Exemplary autoclavable RFID tags include the DASH XSS, DOT XSS, Pico Plus and Roswell made by Xerafy®.

Figure 20B:
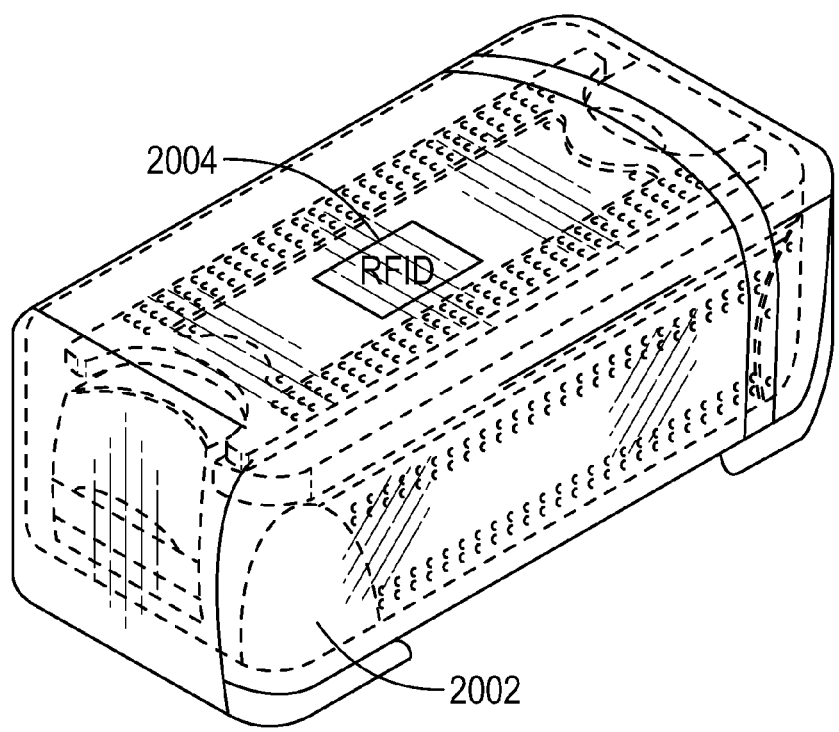
FIG. 20B is a diagram illustrating a sealed wrap over the sterilization case.

As shown in FIG. 20B, the instrument tray case 2002 may be a sealed wrap case. The medical instruments 2102 in tray case 2002 may each also include an RFID tag 2104. The RFID tags 2004, 2104 can send identification and medical data to the DCE upon interrogation. The medical data can include usage data such as the instruments inside the case 2002, expiration date of any medications, a sterilization history and a date and time stamp for the interrogation transaction. Although not shown, the wrap can include its own RFID tag to allow the determination of when the wrap's RFID tag is no longer in proximity to (or has changed in proximity to) the instrument tray's RFID tag 2004 similarly to the medical item 10 shown in FIG. 9A-9B to determine that the instrument tray 2002 is no longer sterile (i.e. has been opened). This is very important in allowing the system to be capable of determining when an instrument tray is contaminated, particularly when the tray is of the variety that does not have a cover, but also in the case where it has a cover which has not been opened (even if cover is on, if wrap has been removed, it is contaminated).

Figure 22:
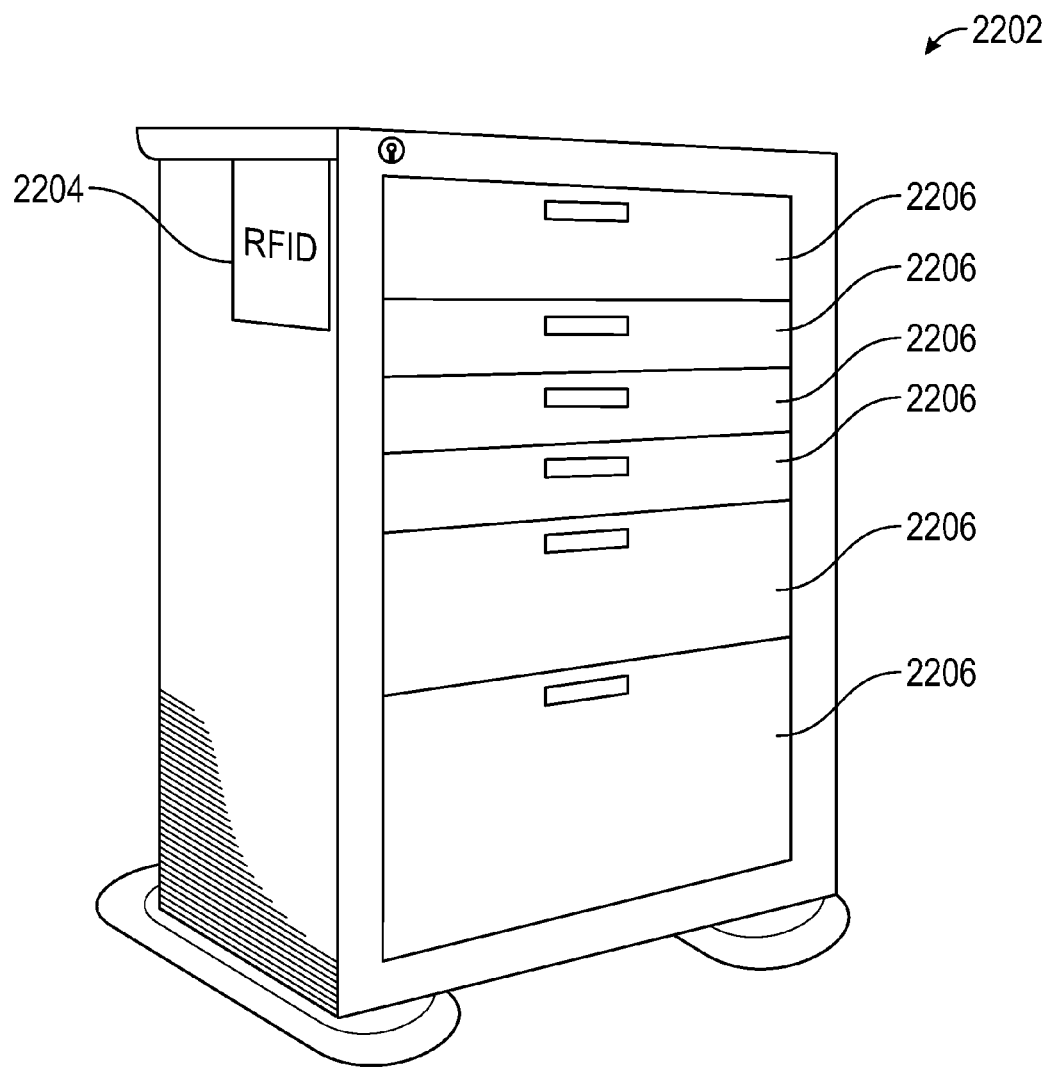
FIG. 22 is a perspective diagram of a medicine storage cabinet including an RFID tag on an outer surface.
Figure 23:
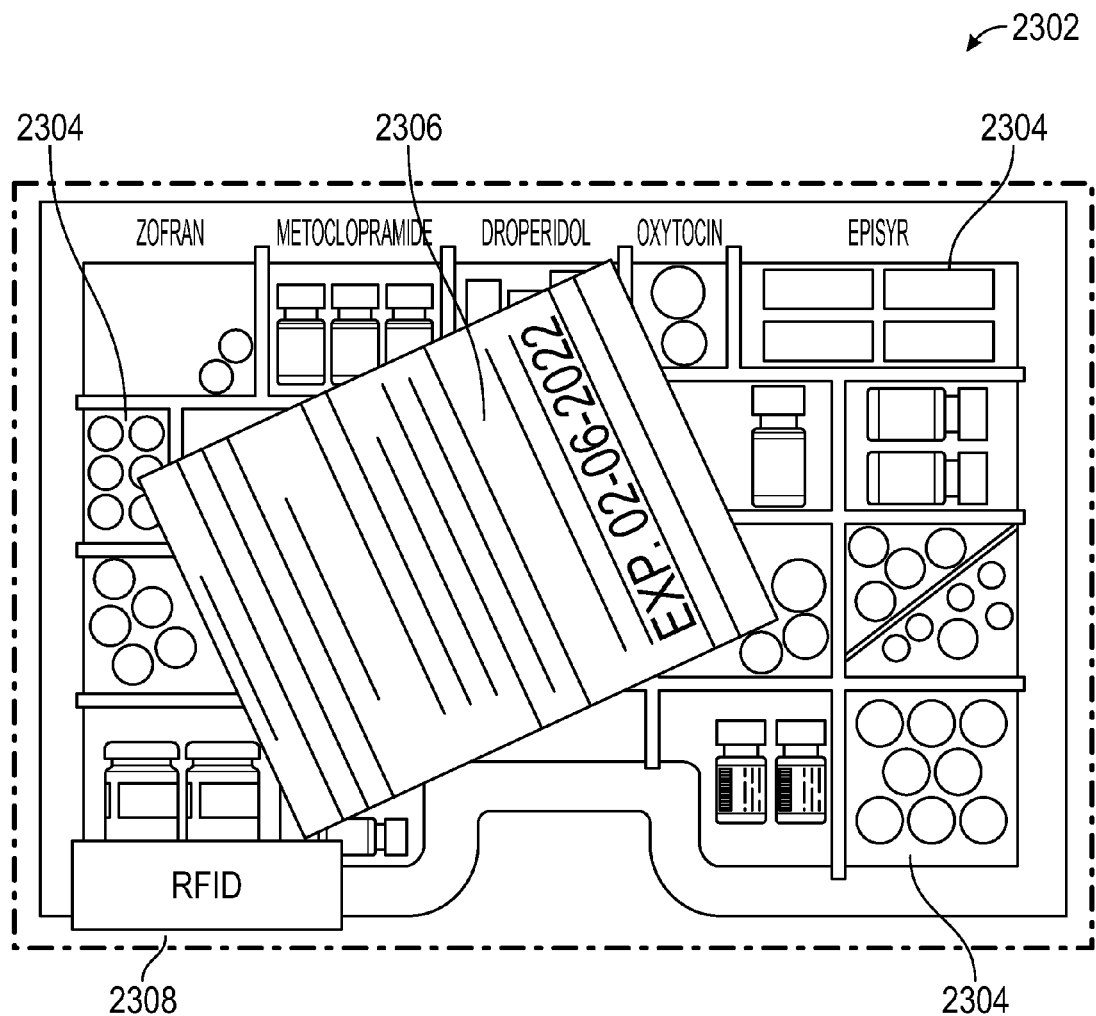
FIG. 23 is diagram illustrating exemplary medicines stored in the medicine storage cabinet.
Figure 24:
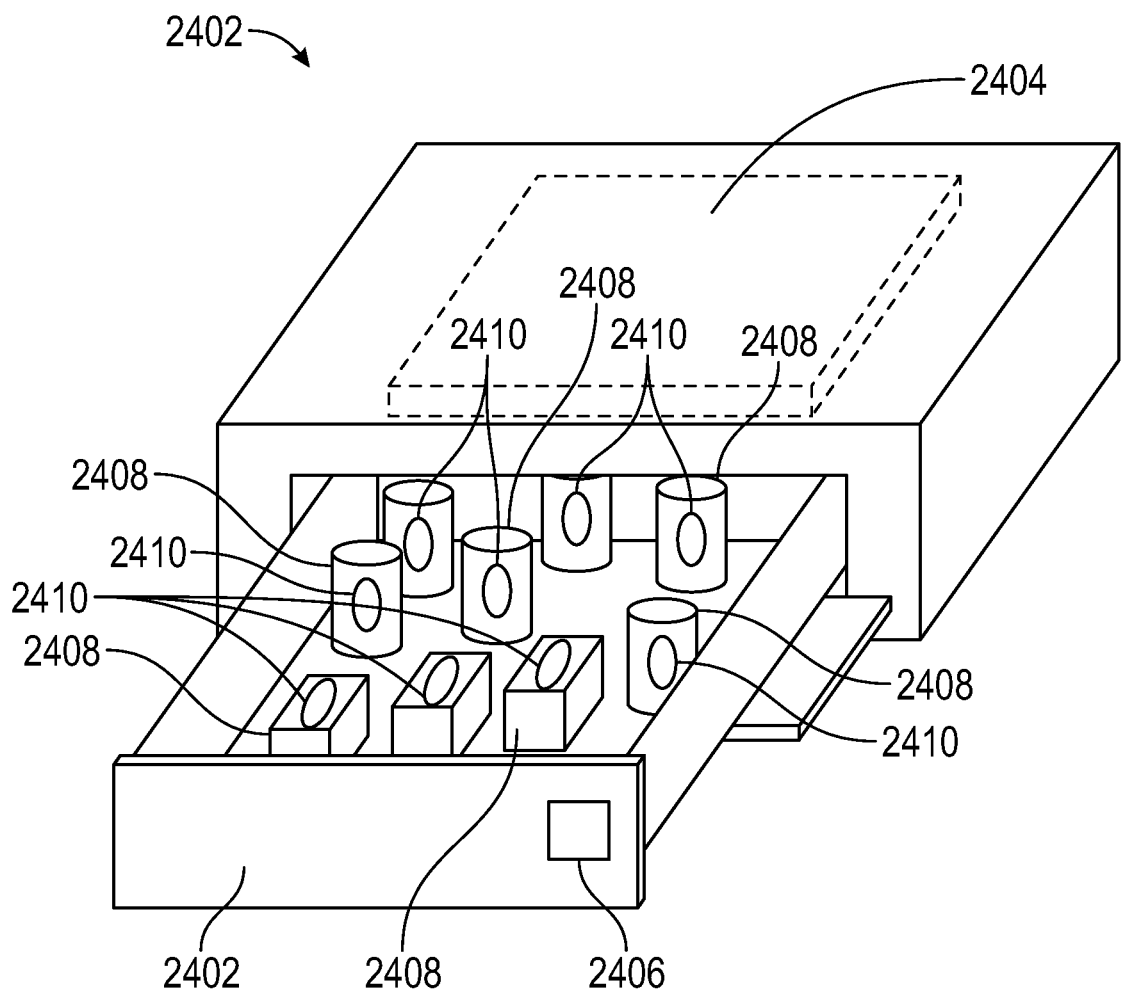
FIG. 24 is a diagram illustrating an opened drawer in the medicine storage cabinet.

Referring to FIG. 22, the medical item can be a medicine storage cabinet 2202 such as a code cart. The cabinet 2202 includes an RFID tag 2204 and a plurality of drawers 2206. Each of the drawers 2206 can include medical instruments as shown in FIG. 21, medicine package 2302 as shown in FIG. 23 or medicines 2408 as shown in FIG. 24. Each of the medical instruments in the drawers 2206 can have their own RFID tags (similarly to FIG. 21).

As shown in FIG. 23, the medicine package 2302 can include a plurality of medicines 2304, a label 2306 indicating an expiration date associated with the medicines 2304 and an RFID tag 2308. The RFID tag 2308 or similar RFID tags on the individual medicines 2410 (similar to 2104 in FIG. 21) can send identification and medical data to a mobile device reader or the DCE upon interrogation. The medical data can include the expiration date indicated in the label 2306. Each medical item 2410, including medical items 2304 in the medicine package 2302, may alternatively have its/their own expiration date(s). Any expiration date(s) may be stored in memory on the respective RFID chip and/or stored in memory on the server, DCE and/or mobile reader device with an identifier which references the respective RFID chip's identity which in turn is referenced to the identity of a specific medical item.

Referring to FIG. 24, a drawer 2402 may include its own DCE or reader depicted by 2404 and an RFID tag 2406 incorporating a sensor such as, for example, an accelerator sensor so that opening of the drawer 2402 can be detected. The drawer 2402 can also include a plurality of medications 2408 which each include an RFID tag 2410. The DCE 2404 can interrogate the RFID tags 2406, 2410 to determine which medicines 2408 are inside the drawer 2402 and when the drawer 2402 is open. Further, the DCE 2404 can determine the identification of an individual such as (returning to FIG. 9D) a medical professional 40 opening the drawer 2402 by interrogating the RFID tag 908 of the medical professional's identification 50 and in addition capturing the proximity of the RFID tag 908 to the DCE 2404 and/or RFID tags 2410.

Figure 25:
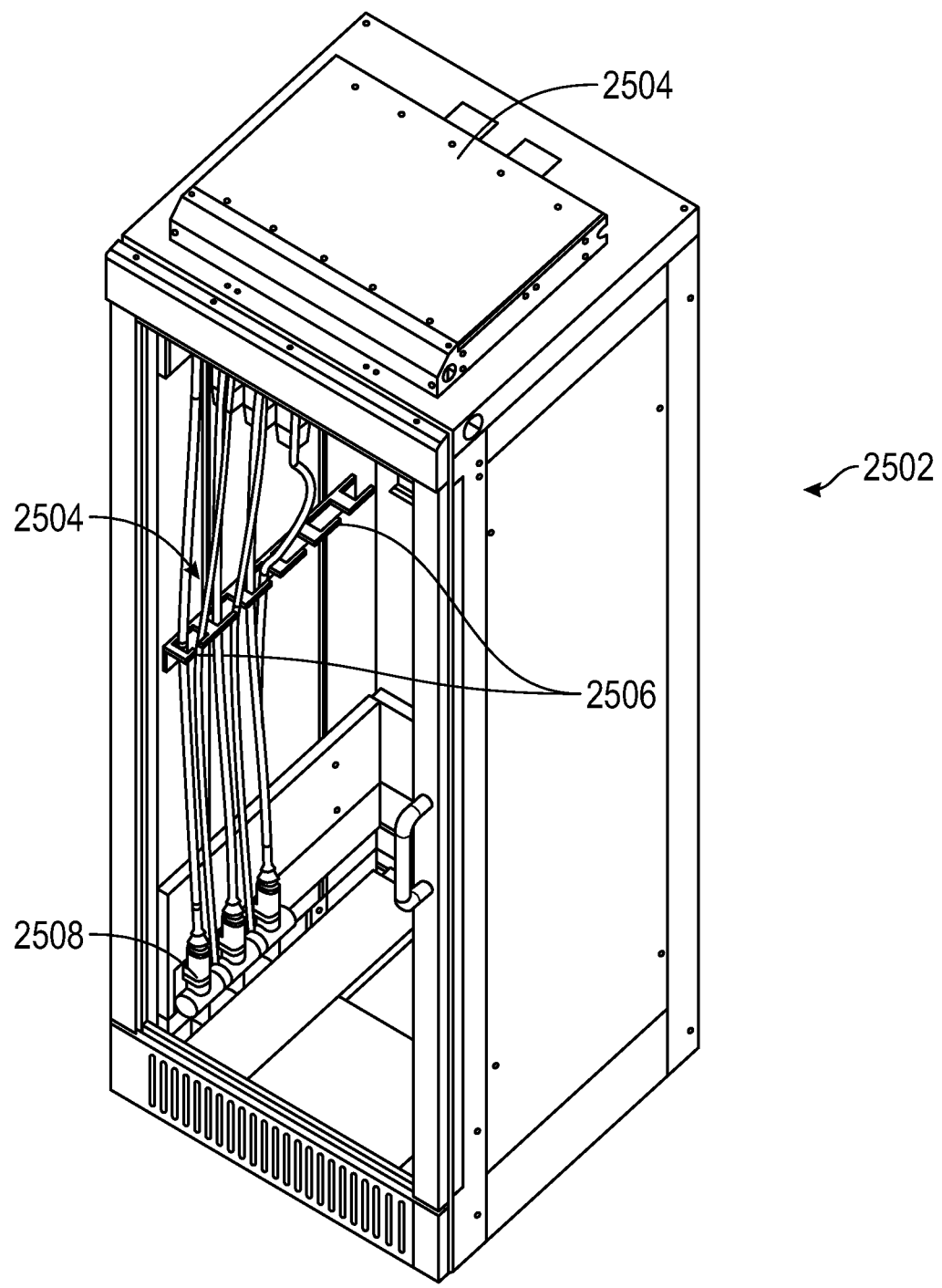
FIG. 25 is a perspective diagram illustrating an exemplary endoscope storage cabinet.

Referring to FIG. 25, the medical item can be an endoscope storage cabinet 2502 similar to as described in U.S. Pat. No. 8,414,471. The cabinet 2502 can include a DCE 2504 on a top portion thereof. A plurality of endoscopes 2504 hang in the cabinet 2506 via retaining portions 2506 and hangers (not shown). Each of the endoscopes 2504 can include an RFID tag 2508. Further, each of the retaining portions 2506 can include an RFID tag which incorporates a sensor portion to detect when the respective endoscope has been removed. The DCE 2504 can interrogate the RFID tags 2508 on the endoscopes 2504 to determine a number in the cabinet 2502. Further, the DCE 2504 can interrogate the RFID tag of a medical professional who accesses the cabinet 2502, capturing data including the proximity of the medical professional's RFID tag 908 and the DCE 2504 and/or any RFID tags 2508, 2504 therein the cabinet 502 and changes in the proximity over time, and the number of endoscopes 2504 before and after the medical professional accesses the cabinet to determine which medical professional used how many of the endoscopes 2504.

Figure 26:
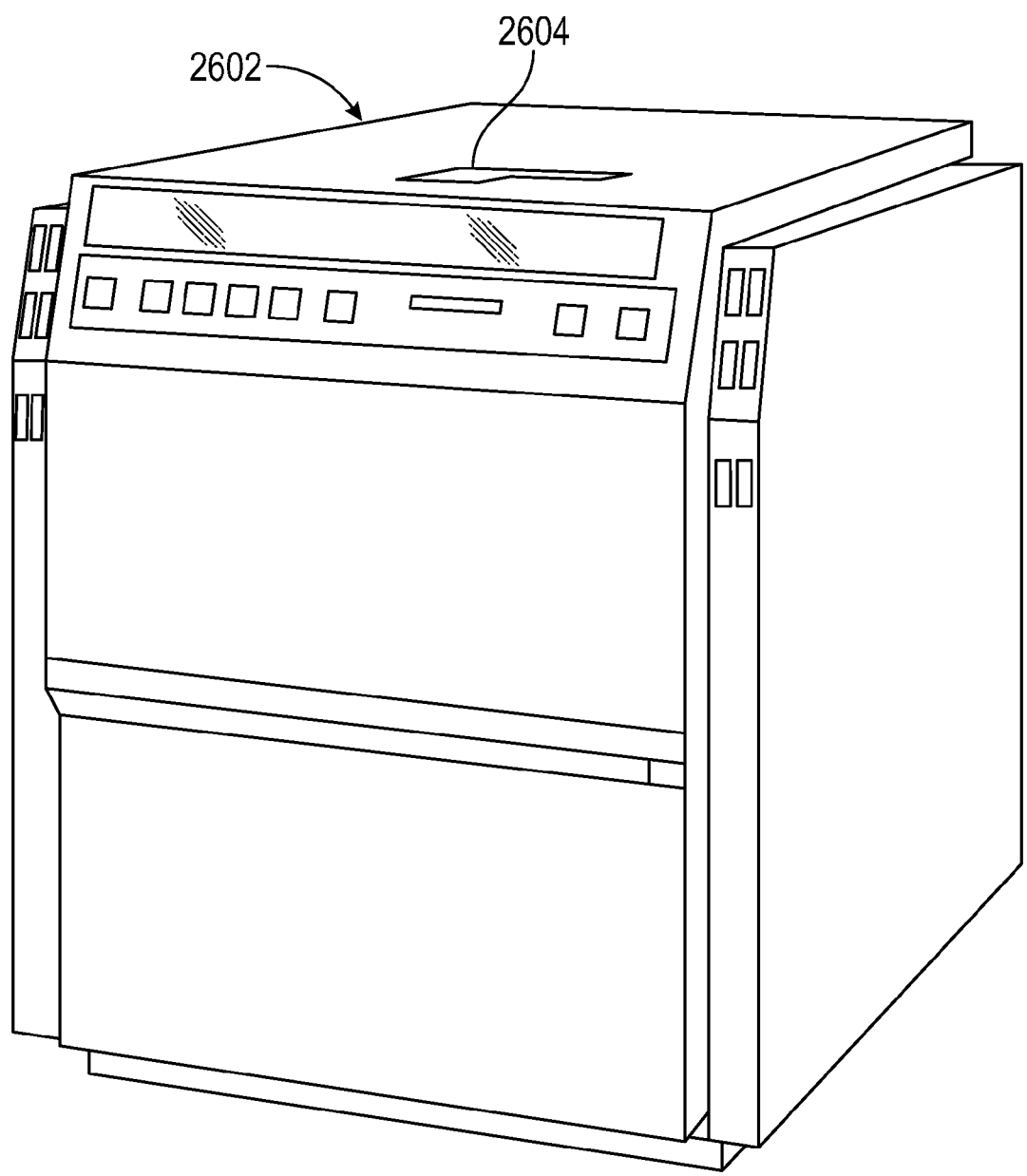
FIG. 26 is a perspective diagram illustrating an exemplary autoclave machine.

Referring to FIG. 26, the medical item 2602 can be an autoclave machine 2602 similar to as described in U.S. Pat. No. 5,535,141 (the contents of which are incorporated herein by reference). The autoclave machine 2602 includes an RFID tag 2604 for communicating with a DCE, for example, similar to DCE 102 shown in FIG. 9A. Alternatively, the autoclave machine 2602 can incorporate its own DCE similar to the endoscope storage cabinet 2504. When a medical item is sterilized by the autoclave machine 2602, the DCE can receive a message indicative of the medical item sterilized and the time it was sterilized from the RFID tag of the medical item or the machine 2602. For example, the RFID tag 2604 can be an active-type RFID tag and the medical item can have a passive-type RFID tag similar to the tags 902, 904 discussed in FIG. 9A. The RFID tag 2604 can include a sensor such as an accelerator sensor to determine when the autoclave machine door has been opened and closed. The RFID tag 2604 can activate the passive-type RFID tag of the medical item when the medical item is inserted in the autoclave machine 2602 by sensing closing of the door. The RFID tag 2604 can then transmit a message to the DCE 102 indicative of the identification of the medical item sterilized and the time it was sterilized. The DCE 102 can then transmit this message to the server device 114. The server device 1110 can store usage parameters associated with the medical item in the database 1108. Particularly, a user can query when the medical item has been sterilized. The database 1108 may include recommended sterilization time periods for each medical item.

When a medical item is sterilized by the autoclave machine 2602, the DCE can receive a message indicative of the medical item sterilized and the time it was sterilized from the RFID tag of the medical item or the machine 2602.

Similar to as shown in FIGS. 1 and 11, the RFID tag 2604 associated with the autoclave machine 2602 can communicate with the server 1110 via the DCE 102. Particularly, the controller 1104 can be configured according to instructions in the memory 1106 to interpret a plurality of RFID reading event derived data obtained from a plurality of interrogations initiated by the DCE over a given period of time which the server 1110 received and stored in its database 1108. At the time of each interrogation/RFID reading event, the DCE can determine the identity of each medical item 2102, RFID chip 2104 and/or medical personnel 40 RFID chip 908 present (in proximity) and interrogated (and that of the autoclave 2604 if applicable) and the proximity between each RFID chip and the DCE or each RFID chip and the autoclave RFID chip 2604; each RFID reading event includes a date and time stamp in addition to other medical data. The change in distance between RFID chips 2410, 2104, 2004 and the DCE and/or RFID chip 2604 in combination with the date and time stamp derived from a series of RFID reading events can be used to determine when the medical items were approaching and subsequently placed in the autoclave, the likely identity of the medical personnel that transported the medical items to the autoclave location, the likely identity of the medical personnel that placed the items in the autoclave, how long each specific medical item remained in the autoclave, when each specific medical item subsequently was moving away from the autoclave indicative of removal from the autoclave, the likely identity of the medical personnel that removed the medical items from the autoclave and the likely identity of the medical personnel that transported the medical items from the autoclave location. In addition, a plurality of temperature sensors associated with the autoclave 2602 and/or the RFID chip 2604 (or communicated with by the RFID chip 2604) can provide a reading of the internal temperature at the time of a reading event. This data in combination with the medical item 2102—autoclave DCE and/or autoclave RFID 2604 proximity data and time stamps and data from readings of the RFID associated with an accelerometer sensor (described below) can be used to determine how long each medical item was exposed to what temperature(s).

Referring to FIG. 27, the medical item can be a refrigerated storage cabinet 2702 similar to as described in U.S. Patent Publication No. 2011/0202170 (the contents of which are incorporated herein by reference). Particularly, the cabinet 2702 can store medical products including medications, tissues, and blood products such as whole blood, plasma, or platelets, for example, which have a limited shelf life and stringent quality control requirements to maintain the quality of the products.

The cabinet 2702 can include its own DCE (depicted by 2704) or alternatively the DCE can be separate similarly to the DCE shown in FIG. 9A. The cabinet 2702 includes an RFID tag 2708 incorporating a plurality of temperature sensors or alternatively communicates with temperature sensors for detecting the internal temperature of the cabinet 2702.

The cabinet 2702 includes a door 2706 with a sensor for detecting when opened. The DCE 2704 can interrogate the RFID tag of identification of the individual who opened the door and send a message indicative of this medical data to the server device. For example, the door 2706 can be configured to hinder access unless individuals with certain privileges (indicated by their RFID tags) are near the RFID tag 2708 (or sufficiently close to be interrogated by the DC 2704). The cabinet 2702 includes a plurality of storage locations 2710 for storing the medical products. Access to the storage locations 2710 can also be configured to be hindered unless individuals with certain privileges (indicated by their RFID tags and/or in combination with a database look up using the unique identifier of their ID badge RFID tag) are near the RFID tag 2708. The DCE 2704 can also be configured and deployed to periodically (every X time interval) interrogate RFID tags in proximity. Data from each DCE interrogation event may be sent by the DCE to the server 1110 immediately or in a batch along with data from other DCE interrogation events at a time after the any specific interrogation event). This data is stored by the server 1110 in the database 1108. Data from a plurality of RFID reading events (interrogations), potentially in combination with data read from the associated cabinet 2702 door 2706 RFID accelerometer sensor, collected over time can be used to determine/predict "net events" that have occurred. For example, the data, including reading event date and time stamps, from a plurality of DCE/RFID tag reading events may predict that medical personnel 40 with a specific identity derived from the individuals ID badge's 50 RFID tag's 908 unique identifier approached the cabinet 2702, DCE 2704, RFID tag 2708, opened the cabinet door 2706, removed a plurality of medical items, for example 2304, 2408, closed cabinet door 2706, moved away from cabinet 2702, DCE 2704, RFID tag 2708 along with medical items 2304, 2408 which remained in proximity to the individual 40 (the individuals ID badge 50 RFID tag 908) while concurrently moving away from the cabinet 2702. The predicted "net event" (medical personnel 50 of a specific identity 908 removed a specific medical item 2304, 2408 from cabinet 2702) is determined by the server using machine learning via its trained neural network models from processing of the plurality of data from the RFID tag reading events and their respective date and time stamps. Further, the RFID tag 2708 monitors the interior temperature and sends a message representative of the interior temperature at specific date and time stamps to the DCE, which forwards this message to the server 1110.

The server 1110 can receive the medical data from the RFIDs of the medical items shown in FIGS. 20A-27. The server 1110 can store the medical data in the database 1108 associated with each medical item or the medical items stored within the medical item. For example, the server 1110 can store an identification for the instrument tray case 2002 and medical data indicative of what instruments are in the case 2002. Accordingly, a user can query the RFID 2004 of the case 2002 and retrieve this information from, for example, the server 114. For example, the server 114 can store an identification for the cart 2002, each drawer 2206 of the cart and medical data indicative of what medical items are in the drawers 2206. Accordingly, a user can query the RFID 2204 of the cart 2202 and retrieve this information from, for example, the server 1110. A similar approach can be used for the endoscope case 2502. Further, when a medical professional accesses one of these medical items or the items therein, the DCE can interrogate the RFID tag associated with the identification of the medical professional so that an access record can be maintained. Changes over time in the specific medical item 2408 RFID tag 2410 identities in proximity (present at the time of a specific interrogation reading) to a cabinet 2402, 2502, 2702 or its associated DCE 2404, 2504, 2704 or RFID tag(s) 2406, 2506, 2508, 2604, 2708 can be used to maintain an inventory record. Further, the server 1110 can store in the database 1108 a time at which each medical item was sterilized in the autoclave machine 2602 or discrete time ranges in combination with internal autoclave temperature readings during that time range denoting a period of autoclaving and a recommended sterilization cycle or minimum sterilization requirements (for example, exposure to a minimum required temperature for a minimum duration of time) for the medical item. Therefore, for example, a user can query the system using a particular medical item RFID tag identity to confirm that the necessary sterilization has taken place.

Returning to FIG. 27, the sensors associated with the RFID tag 2708 of the refrigerated storage cabinet 2702 detect the interior temperature. The DCE 2704 periodically interrogates the tag 2708 and the RFIDs 2410 of any other medical items 2408 in proximity to send a message indicative of the temperature and/or the medical items present, for example 2304, 2408, within the cabinet 2702 and their proximity to the cabinet DCE 2704 an/or the proximity to the cabinet RFID tag 2708 at the time of the interrogation, as medical data to the server 1110 along with the date and time of each interrogation which the server 1110 then stores in the medical database 1108. The server 114 can store in the medical database 1108 associated with the identification for the cabinet 2702 a recommended temperature range (minimum and or maximum required temperature) for each of the medical items stored in the cabinet 2702. Therefore, the server 1110 can notify a medical professional when the cabinet 2702 needs to be maintained or when the medical items in the cabinet cannot be used.

In the examples shown in FIGS. 20A-27, another RFID tag storing a unique location information can be affixed to a room. The server can receive this location identification from this RFID tag directly or via a DCE or reader. The server can store a location database in which medical items at locations are entered. Further, the RFID tags can include Global Position System (GPS) capability so that the medical data sent to the server includes location information.

The DCE discussed in these alternative embodiments can also be or include a device reader such as a smartphone 502 shown in FIG. 5 or fixed gateway readers such as, for example, the XARRAY, XSPAN and XPORTAL made by IMPINJ™ or fixed and handheld readers such as the SPEEDWAY R420, SPEEDWAY R220, SPEEDWAY R120, ATID AB700 and TSL 1128 also made by IMPINJ™. The DCE can include chips such as the INDY series chip (INDY RS2000, INDY RS1000, INDY RS500, INDY R2000 or INDY R500, etc.) also made by IMPINJ™ and Returning to FIGS. 9A-9G, the illustrated scenario is also similar to the process when, for example, the sterilization case shown in FIGS. 20A-20B is opened. The server device can predict consumption of the medical item as shown in FIG. 9G based upon a trained NNM as discussed below.

Utilizing Machine Learning

As mentioned above, the server device 1110 (or DCE 102) can utilize machine learning algorithms to predict events related to, for example, the position and state of the medical items and changes thereof over time. For example, a trained model can be used to predict when the medicine in the cabinet 2702 is at risk of becoming in an unusable state due to for, example, storage for a particular duration at a temperature too high. For example, the risk that medical item(s) may be spoiled (no longer suitable for use) can be predicted from the medical item identities, temperature data collected over time from cabinet 2702 in combination with the known required storage criteria for said medical items (derived by proxy from NNM training set data where medications of specific types were determined to be spoiled after a period of storage at a plurality of temperatures) trained model. Similarly the trained models can make predictions of other "net events" using knowledge derived from NNM training data such as removal of a specific medical item from a cabinet 2402, 2502, 2702, instrument tray 2002 or other medical item by a specific medical worker, successful or compliant sterilization of a medical item (autoclaved for a minimum duration of time above a minimum temperature), medical items that may pose a patient safety threat if used because they were inappropriately stored (i.e. at wrong temperature), potential use of a medical item by a medical worker when said medical item may pose a safety risk to a patient (item is expired, item has not been appropriately sterilized, or item was stored improperly, such as at the wrong temperature). In one exemplary case say the safety for usage of a medicine requiring storage within a specific temperature range stored in a cabinet, the server device can train the NNM to generate an output value to make this prediction.

Creation of the NNM

In this case, a NNM, which includes an input layer, one or more hidden layers and an output layer is initialized. The input layer includes a number of input neurons in accordance with the plurality of input attributes, the output layer including a number of output neurons in accordance with the quantifiable outcome, and each of the one or more hidden layers including a number of hidden layers with a plurality of hidden neurons and possibly a bias neuron. The controller is configured to initialize values of a plurality of synaptic weights of the NNM to random values. In this case, the input attributes can be temperature values, RFID tag identities (i.e. which are proxies for: the identities of the medical cabinet, potentially the location at which the data was collected, medical items in the medical cabinet, etc.), related respective specific identity of medicines (i.e. amoxicillin suspension with a specific lot number and a specific numbered vial, package, such as blister package, label, syringe, or other identifier) that map to the RFID IDs of the medical items in the cabinet which were interrogated, related sensor temperature reading values and time values associated with the data derived from each interrogation event of the RFID tags from which the data is derived.

Each of the plurality of hidden neurons includes an activation function, the activation function can be one of: (1) the sigmoid function $f(x)=1/(1+e^{-x})$; (2) the hyperbolic tangent function $f(x)=(e^{2x}-1)/(e^{2x}+1)$; and (3) a linear function $f(x)=x$, wherein x is a summation of input neurons biased by the synoptic weights The NNM is one or more of a feed forward structure Neural Network; ADALINE Neural Network, Adaptive Resonance Theory 1 (ART1), Bidirectional Associative Memory (BAM), Boltzmann Machine, Counterpropagation Neural Network (CPN), Elman Recurrent Neural Network, Hopfield Neural Network, Jordan Recurrent Neural Network, Neuroevolution of Augmenting Topologies (NEAT), and Radial Basis Function Network.

To train and validate the NNM, a plurality of past patient cabinet risk state events with known outcomes are needed. For example, a data set associated with known medication discontinuance (cabinet internal temperature associated spoilage of medicine) is needed. The data set can include temperature values, medication characteristics, etc. and changes therein overtime (i.e. time series data). The data set can be divided into a first set of training data and a second set of validation data.

Training of the NNM

To train the NNM, the controller iteratively performs a machine learning algorithm (MLA) to adjust the values of the synaptic weights until a global error of an output of the NNM is below a predetermined acceptable global error. Performing of the MLA includes: generating an output value of the NNM for each past medication risk state event of the training data based upon the input attributes; measuring the global error of the NNM based upon the output values of the NNM and the quantifiable outcomes of the past event; and adjusting the values of the synaptic weights if the measured global error is not less than the predetermined acceptable global error to thereby obtain a trained NNM. Here, if the global error is never reached after number of outcomes, the model can be revised, such as number of hidden layers, neurons, etc.

Validating of the NNM

To validate the NNM, the controller generates an output value of the trained NNM for each past risk state events of the validation data, wherein each of the output values represents a calculated quantifiable outcome of the respective event; and determines if the output values correspond to the quantifiable outcome within the predetermined global error.

The creation and training of the NNM can be repeated until validation data results are satisfactory, defined as output data from the NNM being within the acceptable level of global error from the output values in the validation data set.

Using the Trained NNM

The controller conducts pre-processing of input attributes of the new data. The input attributes can be, for example, RFID tag identifier, medicine package identifier, and temperature as mentioned above. The controller generates an output value of the trained NNM based upon the input attributes of the new event. The input attributes will contain temperature measurements and the medicines in the cabinet. The output value can be a prediction of whether the medicine cannot be used as determined from prior data collected from the cabinet, including the medications within it and the internal cabinet temperature at the time of specific reading or interrogation events, and RFID tags of the cabinet. Finally, the server device can use the trained NNM to predict whether the current data within the context of data previously collected over time are consistent with particular outcomes (i.e. use of a specific medicine in cabinet poses a significant risk to patient).

The MLA for updating the synoptic weights is one or more of ADALINE training, backpropagation algorithm, competitive learning, genetic algorithm training, Hopfield learning, Instar and Outstar training, the Levenberg-Marquardt algorithm (LMA), Manhattan Update Rule Propagation, Nelder Mead Training, Particle Swarm (PSO) training, quick propagation algorithm, resilient propagation (RPROP) algorithm, scaled conjugate gradient (SCG), support vector machines, genetic programming, Bayesian statistics, decision trees, case based reasoning, information fuzzy networks, clustering, hidden Markov models, particle swarm optimization, simulated annealing.

While only certain features of the invention have been illustrated and described herein, many modifications and changes will occur to those of ordinary skill in the art. The following claims are intended to cover all such modifications and changes.

What is claimed is:

1. A system comprising:
    a medical storage unit including a first radio-frequency identification (RFID) chip, the medical storage unit storing a plurality of medical items, wherein each of the plurality of medical items includes a second RFID chip,
    wherein at least the first RFID chip includes:
        a controller configured according to instructions in memory to generate a message including identification information associated with the respective RFID chip and medical data; and
        an antenna portion configured to transmit the message;
    a reader device communicating with the at least one of the first RFID chip and the second RFID chip, wherein the reader device comprises:
        a transceiver configured to receive the message from the at least one of the first RFID chip and the second RFID chip;
        a controller operatively coupled to the transceiver; and
        one or more memory sources operatively coupled to the controller, the one or more memory sources including instructions for configuring the controller to generate one or more messages indicative of the identification information and the medical data to be sent by the transceiver to a server device via a network connection;
    wherein the server device comprises:
        a transceiver configured to receive the one or more messages from the reader device;
        a controller operatively coupled to the transceiver; and
        one or more memory sources operatively coupled to the controller, the one or more memory sources storing:
            a first database including a plurality of states for the medical storage unit and attributes for each of the plurality of states;
            a trained neural network model (NNM) for generating an output value based upon the medical data; and
            instructions for configuring the controller to determine whether the output value corresponds with one or more of the attributes associated with one or more of the states in the first database.

2. The system of claim 1, wherein the controller of the server device is further configured to:

perform pre-processing on the medical data to generate an input data set; and
generate the output value from the trained model based upon the input data set.

3. The system of claim 1, wherein in the server device:
the one or more memory sources further store a plurality of past risk state events, each of the plurality of past risk state events including a plurality of attributes and a quantifiable outcome; and
the controller is further configured to:
train a neural network model (NNM) to generate the trained NNM, wherein the training of the NNM includes:
performing pre-processing on the plurality of attributes for each of the plurality of past risk state events to generate a plurality of input data sets;
dividing the plurality of past risk state events into a first set of training data and a second set of validation data;
iteratively performing a machine learning algorithm (MLA) to update synaptic weights of the NNM based upon the training data; and
validating the NNM based upon the second set of validation data,
wherein the MLA for updating the synoptic weights is one or more of ADALINE training, backpropagation algorithm, competitive learning, genetic algorithm training, Hopfield learning, Instar and Outstar training, the Levenberg-Marquardt algorithm (LMA), Manhattan Update Rule Propagation, Nelder Mead Training, Particle Swarm (PSO) training, quick propagation algorithm, resilient propagation (RPROP) algorithm, scaled conjugate gradient (SCG), support vector machines, genetic programming, Bayesian statistics, decision trees, case based reasoning, information fuzzy networks, clustering, hidden Markov models, particle swarm optimization, simulated annealing.

4. The system of claim 3, wherein:
the NNM includes an input layer, output layer, and a plurality of hidden layers with a plurality of hidden neurons; and
each of the plurality of hidden neurons includes an activation function, the activation function is one of:
(1) the sigmoid function $f(x)=1/(1+e^{-x})$;
(2) the hyperbolic tangent function $f(x)=(e^{2x}-1)/(e^{2x}+1)$; and
(3) a linear function $f(x)=x$,
wherein x is a summation of input neurons biased by the synoptic weights.

5. The system of claim 3, wherein the NNM is one or more of a feed forward structure Neural Network; ADALINE Neural Network, Adaptive Resonance Theory 1 (ART1), Bidirectional Associative Memory (BAM), Boltzmann Machine, Counterpropagation Neural Network (CPN), Elman Recurrent Neural Network, Hopfield Neural Network, Jordan Recurrent Neural Network, Neuroevolution of Augmenting Topologies (NEAT), and Radial Basis Function Network.

6. The system of claim 1, wherein the plurality of states for the medical storage unit include expiration dates for each of the medical items.

7. The system of claim 1, wherein the plurality of states for the medical storage unit include cleaning and maintenance cycles for each of the medical items.

8. A system comprising:
a medical item including a plurality of radio-frequency identification (RFID) chips, wherein at least a first RFID chip of the plurality of RFID chips is a passive-type RFID chip with no battery, wherein at least one of the first RFID chip and a second RFID chip of the plurality of RFID chips includes:
a controller configured according to instructions in memory to generate a message including identification information and medical data associated with the respective RFID chip; and
an antenna portion configured to transmit the message;
wherein the first RFID chip includes an antenna for wirelessly receiving power from a power transmission subsystem;
a device reader communicating with the at least one of the first RFID chip and the second RFID chip, wherein the device reader comprises:
a transceiver configured to receive the message from the at least one of the first RFID chip and the second RFID chip;
a controller operatively coupled to the transceiver; and
one or more memory sources operatively coupled to the controller, the one or more memory sources including instructions for configuring the controller to generate one or more messages indicative of the identification information and medical data to be sent by the transceiver to a server device via a network connection,
wherein the server device comprises:
a transceiver configured to receive the one or more messages from the device reader, the first RFID chip or the second RFID chip;
a controller operatively coupled to the transceiver; and
one or more memory sources operatively coupled to the controller, the one or more memory sources storing:
a first database including a plurality of identification of medical items and usage parameters for each of the medical items; and
instructions for configuring the controller to determine data in the medical item database that is associated with the identification for the at least one of the first RFID chip and the second RFID chip; and
generate an information reply including usage parameters associated with the medical item based upon the determined data, the usage parameters include an identification of a medical professional that used the medical item and an identification of a patient for whom the medical item was used.

9. The system of claim 8, wherein the usage parameters include an expiration date or temperature parameter associated with the medical item.

10. The system of claim 8, wherein the usage parameters include a cleaning and maintenance cycle of the medical item.

11. The system of claim 8, wherein the usage parameters include location data of the medical item.

12. A server device comprising:
a transceiver configured to receive one or more messages from a mobile device or a data collection engine (DCE), the one or more messages generated from an RFID chip and including identification information and medical data for a medical item;
a controller operatively coupled to the transceiver; and
one or more memory sources operatively coupled to the controller, the one or more memory sources storing:

a first database including a plurality of identifications of medical items and usage parameters for each of the medical items; and instructions for configuring the controller to determine data in the medical item database that is associated with the identification information from the RFID chip; and generate an information reply including usage parameters associated with the medical item based upon the determined data.

13. The server device of claim 12, wherein the usage parameters include an identification of a medical professional that used the medical item and an identification of a patient for whom the medical item was used.

14. The server device of claim 12, wherein the usage parameters include an expiration date of the medical item.

15. The server device of claim 12, wherein the usage parameters include a cleaning and maintenance cycle of the medical item.

16. The server device of claim 12, wherein the usage parameters include location data of the medical item.

17. The server device of claim 12, wherein the usage parameters include a detail of medical instruments included in the medical item.

18. The server device of claim 12, wherein the transceiver receives an information query from a remote device and to send the information reply to the remote device.

\* \* \* \* \*